US008818499B2

(12) United States Patent
Karo et al.

(10) Patent No.: US 8,818,499 B2
(45) Date of Patent: Aug. 26, 2014

(54) BODY FAT MEASUREMENT DEVICE

(75) Inventors: Hiromichi Karo, Kyoto (JP); Takehiro Hamaguchi, Kyoto (JP); Kazuhisa Tanabe, Kyoto (JP); Yasuaki Murakawa, Kyoto (JP); Tomoya Ijiri, Kameoka (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/607,080

(22) Filed: Sep. 7, 2012

(65) Prior Publication Data

US 2013/0023747 A1 Jan. 24, 2013

Related U.S. Application Data

(63) Continuation of application No. PCT/JP2011/052267, filed on Feb. 3, 2011.

(30) Foreign Application Priority Data

Mar. 25, 2010 (JP) .................................. 2010-070375

(51) Int. Cl.
*A61B 5/053* (2006.01)
*A61B 5/107* (2006.01)
*A61B 5/00* (2006.01)

(52) U.S. Cl.
CPC ....... *A61B 5/6843* (2013.01); *A61B 2560/0468* (2013.01); *A61B 5/6829* (2013.01); *A61B 5/6823* (2013.01); *A61B 5/6825* (2013.01); *A61B 5/4872* (2013.01); *A61B 5/1072* (2013.01); *A61B 5/0537* (2013.01)
USPC ............ 600/547; 600/382; 600/386; 600/393

(58) Field of Classification Search
USPC ......... 600/300, 301, 547, 587, 382, 384, 386, 600/393; 73/488; 33/227, 783
See application file for complete search history.

(56) References Cited

U.S. PATENT DOCUMENTS 8,494,609 B2 * 7/2013 Karo et al. ..................... 600/382
8,498,687 B2 * 7/2013 Karo et al. ..................... 600/382
(Continued)

FOREIGN PATENT DOCUMENTS

| CN | 1679442 A | 10/2005 |
|---|---|---|
| CN | 101641046 A | 2/2010 |

(Continued)

OTHER PUBLICATIONS

International Search Report issued in International Patent Application No. PCT/JP2011/052267 dated Apr. 19, 2011.

(Continued)

*Primary Examiner* — Max Hindenburg
*Assistant Examiner* — John Pani
(74) *Attorney, Agent, or Firm* — Oliff PLC

(57) ABSTRACT

A body fat measurement device includes hand electrodes that contact both hands, back area electrodes that contact the surface of a trunk area of the back, foot electrodes that contact both feet, a trunk area width detection unit for measuring the width and depth of the trunk area, a body impedance measurement unit that measures the body impedance of a body using the multiple electrodes and a body fat mass calculation unit that calculates a body fat mass based on the body impedance and the width and depth of the trunk area. The back area electrodes that make contact with the surface of the back of the trunk area are provided in a fitting unit in an exposed state, as well as the trunk area width detection unit. Accordingly, a body fat measurement device can measure a body fat mass easily and accurately in a household or the like.

10 Claims, 22 Drawing Sheets

(56) References Cited

U.S. PATENT DOCUMENTS

| | | | |
|---|---|---|---|
| 2004/0077969 A1* | 4/2004 | Onda et al. | 600/547 |
| 2005/0222516 A1* | 10/2005 | Kasahara et al. | 600/547 |
| 2006/0282005 A1* | 12/2006 | Kasahara et al. | 600/547 |
| 2009/0024053 A1* | 1/2009 | Kasahara | 600/547 |
| 2009/0076340 A1* | 3/2009 | Libbus et al. | 600/301 |
| 2010/0081962 A1 | 4/2010 | Hamaguchi et al. | |
| 2011/0137199 A1* | 6/2011 | Karo et al. | 600/547 |

FOREIGN PATENT DOCUMENTS

| | | |
|---|---|---|
| CN | 101677779 A | 3/2010 |
| JP | A-2002-369806 | 12/2002 |
| JP | A-2005-288023 | 10/2005 |
| JP | A-2007-14664 | 1/2007 |
| JP | A-2008-23232 | 2/2008 |
| JP | A-2008-228890 | 10/2008 |
| JP | A-2008-237571 | 10/2008 |
| JP | A-2009-22482 | 2/2009 |
| WO | WO 2008/123044 A1 | 10/2008 |
| WO | WO 2010032835 A1 * | 3/2010 |

OTHER PUBLICATIONS

May 23, 2014 Office Action issued in Chinese Application No. 201180015486.0 (w/ English Translation).

* cited by examiner

BODY FAT MEASUREMENT DEVICE

This is a Continuation of Application No. PCT/JP2011/052267 filed Feb. 3, 2011, which claims the benefit of Japanese Patent Application No. 2010-070375 filed Mar. 25, 2010. The disclosure of the prior applications is hereby incorporated by reference herein in its entirety.

TECHNICAL FIELD

The present invention relates to body fat measurement devices configured so as to be capable of calculating the body fat mass of a measurement subject by measuring a body impedance, and particularly relates to body fat measurement devices configured so as to be capable of easily measuring a visceral fat mass and/or a subcutaneous fat mass in households or the like.

BACKGROUND ART

In recent years, fat mass is gaining attention as an indicator used to determine the health of a measurement subject. In particular, visceral fat mass is gaining attention as an indicator for determining whether or not a person is suffering from central obesity. Central obesity is said to bring about lifestyle-related diseases that can easily lead to artery hardening, such as diabetes, hypertension, and hyperlipidemia, and the stated indicators hold promise in terms of preventing such diseases. "Visceral fat" refers to fat that accumulates around the internal organs on the inner side of the abdominal muscles and the back muscles, and is distinct from the subcutaneous fat that is located toward the surface of the trunk area. It is typical to employ the area occupied by visceral fat in a cross-section of the trunk area that corresponds to the navel (referred to as a "visceral fat cross-sectional area" hereinafter) as an indicator of the visceral fat mass.

Image Analysis Technique

Normally, visceral fat mass is measured by analyzing images obtained through X-ray computed tomography (CT), magnetic resonance imaging (MRI), or the like. In such image analysis, the visceral fat cross-sectional area is calculated geometrically from a tomographic image of the trunk area obtained by using X-ray CT, MRI, or the like. However, it is necessary to use several pieces of large equipment installed in a medical facility, such as X-ray CT, MRI, or other machines, in order to make use of such a measurement method; thus it is extremely difficult to measure visceral fat mass on a daily basis through such a measurement method. X-ray CT also poses the problem of exposure to radiation, and thus cannot necessarily be called a desirable measurement method.

Body Impedance Technique

A body impedance technique is being considered as an alternative to these measurement methods. The body impedance technique is a method for measuring body fat mass widely used in household-based body fat measurement devices; in this technique, electrodes are placed in contact with the four limbs, the body impedance is measured using those electrodes, and the body fat mass is calculated from the measured body impedance. The stated body fat measurement device makes it possible to accurately measure the extent of body fat buildup throughout the entire body or in specific areas such as the four limbs, the trunk area, or the like.

However, conventional body fat measurement devices that use the body impedance technique measure the extent of body fat buildup throughout the entire body or in specific areas such as the four limbs, the trunk area, or the like, as mentioned earlier, and are not capable of accurately extracting and measuring the extent of visceral fat buildup, the extent of subcutaneous fat buildup, and the like individually. This is because, as mentioned above, conventional body fat measurement devices are configured so that the electrodes are attached only to the four limbs, and thus the visceral fat and subcutaneous fat cannot be accurately measured individually.

Accordingly, bringing electrodes into direct contact with the trunk area, measuring the body impedance using those electrodes, and individually and accurately calculating the visceral fat mass and the subcutaneous fat mass based on that measurement is being considered as a way to solve this problem.

For example, JP 2002-369806A (Patent Literature 1) discloses a body fat measurement device configured so that electrodes are provided on the inner circumferential surface of a belt member and the belt member is wrapped around and anchored to the trunk area of a measurement subject, thus placing the electrodes in contact with the trunk area.

Meanwhile, JP 2005-288023A (Patent Literature 2), JP 2008-23232A (Patent Literature 3), JP 2008-237571A (Patent Literature 4), and so on disclose body fat measurement devices configured so that electrodes are provided on the surface of a fitting unit that is fitted to the abdominal area of a measurement subject and the fitting unit is pressed against the abdominal area, thus placing the electrodes in contact with the abdominal area.

Furthermore, JP 2007-14664A (Patent Literature 5) discloses a body fat measurement device configured so that the device is divided into a fitting unit that is fitted to the abdominal area of a measurement subject and a platform unit for the measurement subject to stand upon, where abdominal area electrodes are provided on the surface of the fitting unit, hand electrodes are provided on a handle portion of the fitting unit, and foot electrodes are provided on the stated platform unit; the hand electrodes are placed in contact with the measurement subject's palms by the measurement subject gripping the handle portion of the fitting unit, the abdominal area electrodes are placed in contact with the abdominal area by the measurement subject pressing the fitting unit against his or her abdominal area using the hands that grip the handle portion, and the foot electrodes are placed in contact with the soles of the measurement subject's feet by the measurement subject standing upon the platform unit.

In addition, although not discussing a specific device configuration, JP 2008-228890A (Patent Literature 6) mentions being able to accurately measure visceral fat mass and subcutaneous fat mass by placing electrodes in contact with the back of a measurement subject's trunk area (that is, the back) without placing electrodes in contact with the measurement subject's abdominal area and placing electrodes in contact with the hands and feet of the measurement subject, measuring the body impedance, and calculating the visceral fat mass and the subcutaneous fat mass based on the measured body impedance.

Meanwhile, to make it possible to measure the visceral fat mass, subcutaneous fat mass, and so on with a high degree of accuracy using the stated body impedance, it is necessary to take actual measurements of the measurement subject's body build, such as the circumferential length of the trunk area, the trunk area width, and the trunk area depth, and use the measurements in computation processes for calculating the body fat mass.

For example, according to the body fat measurement device disclosed in the stated JP 2005-288023A (Patent Literature 2), a fitting unit that is fitted to a measurement subject's abdominal area is provided upon a pair of arm portions, which make contact with both sides of the measurement subject's trunk area (in other words, both flanks), so that the fitting unit is mobile; the trunk area width is measured by bringing the arm portions into contact with both flanks, and the result of that actual measurement is used in computation processes for calculating body fat mass.

Meanwhile, according to the body fat measurement device disclosed in the stated JP 2008-23232A (Patent Literature 3), a fitting unit that is fitted to a measurement subject's abdominal area is provided upon an arm portion, which makes contact with the measurement subject's back, so that the fitting unit is mobile; the trunk area depth is measured by bringing the arm portion into contact with the back, and the result of that actual measurement is used in computation processes for calculating body fat mass.

Furthermore, according to the body fat measurement device disclosed in the stated JP 2008-237571A (Patent Literature 4), a trunk area width measurement unit disposed at a distance from the outside of both sides of the measurement subject's trunk area is configured separate from a fitting unit that is fitted to the measurement subject's abdominal area, and multiple non-contact range sensors are provided in the trunk area width measurement unit so as to take an actual measurement of the trunk area width; the result of that actual measurement is used in computation processes for calculating body fat mass.

Furthermore, although the technique does not bring electrodes into contact with a measurement subject's trunk area, JP 2009-22482A (Patent Literature 7) discloses a body fat measurement device in which foot electrodes are provided on a platform unit onto which the measurement subject steps, a trunk area width measurement unit disposed at a distance from the outside of both sides of the measurement subject's trunk area is supported on a support column portion that extends upward from the stated platform unit while the measurement subject stands on the platform unit, and multiple non-contact range sensors are provided in the trunk area width measurement unit so as to take an actual measurement of the trunk area width; the result of that actual measurement is used in computation processes for calculating body fat mass.

CITATION LIST

Patent Literature

Patent Literature 1: JP 2002-369806A
Patent Literature 2: JP 2005-288023A
Patent Literature 3: JP 2008-23232A
Patent Literature 4: JP 2008-237571A
Patent Literature 5: JP 2007-14664A
Patent Literature 6: JP 2008-228890A
Patent Literature 7: JP 2009-22482A

SUMMARY OF INVENTION

Technical Problem

Here, in order to realize a body fat measurement device configured to be capable of easily and accurately calculating visceral fat mass and subcutaneous fat mass at home using the body impedance technique, it is extremely important to meet the following two conditions: one, that the measurement can be performed easily through simple operations; and two, that the measurement subject can perform the measurement him/herself without help from an assistant or the like. In light of this, it is unrealistic for the measurement subject to lie face up or face down during the measurement; it is preferable to employ a configuration in which the measurement can be carried out from a standing or seated position. Therefore, employing a measurement position as disclosed in the stated JP 2002-369806A (Patent Literature 1), JP 2007-14664A (Patent Literature 5), and JP 2009-22482A (Patent Literature 7) is favorable in terms of realizing a body fat measurement device for household use.

However, as disclosed in the stated JP 2008-228890A (Patent Literature 6), it is necessary to place electrodes in contact with the measurement subject's back without placing electrodes in contact with the measurement subject's abdominal area and to place electrodes in contact with the hands and feet of the measurement subject in order to calculate the visceral fat mass and the subcutaneous fat mass is a more accurate manner. One of the reasons for this is that the subcutaneous fat that accumulates on the abdominal area side is relatively thinner than the subcutaneous fat that accumulates on the back area side, and thus if the electrodes are placed in contact with the abdominal area, the current that is applied will flow through fat-free areas, which makes it easy for errors to occur.

However, the body fat measurement device disclosed in the stated JP 2002-369806A (Patent Literature 1) does not take into consideration placing electrodes in contact with the hands and feet, whereas the body fat measurement device disclosed in the stated JP 2007-14664A (Patent Literature 5) does not take into consideration placing electrodes in contact with the back; meanwhile, the body fat measurement device disclosed in the stated JP 2009-22482A (Patent Literature 7) does not take into consideration placing electrodes in contact with the hands and trunk area at all. Thus it is necessary to make some kind of improvement in order to realize a body fat measurement device capable of easily and accurately calculating visceral fat mass and subcutaneous fat mass at home while employing the measurement method disclosed in the stated JP 2008-228890A (Patent Literature 6).

Meanwhile, to make it possible to more accurately measure the visceral fat mass and subcutaneous fat mass, it is necessary to take actual measurements of the measurement subject's body build, such as the circumferential length of the trunk area, the trunk area width, and the trunk area depth as described above; however, the body fat measurement device disclosed in the stated JP 2002-369806A (Patent Literature 1) does not take into consideration taking actual measurements of the body build, while the body fat measurement devices disclosed in the stated JP 2007-14664A (Patent Literature 5) and JP 2009-22482A (Patent Literature 7) have configurations in which the fitting unit and platform unit are separate units and the trunk area width detection unit used for detecting the trunk area width is provided, and thus there is a problem in that the sizes of the devices are increased and the device configurations are complex. Thus, from this standpoint as well, it is necessary to make some kind of improvement in order to realize a body fat measurement device capable of easily and accurately calculating visceral fat mass and subcutaneous fat mass at home while employing the measurement method disclosed in the stated JP 2008-228890A (Patent Literature 6).

Having been achieved in order to solve the stated problems, it is an object of the present invention to provide a body fat measurement device capable of easily and accurately measuring body fat masses, such as visceral fat mass, even at home.

Solution to Problem

A body fat measurement device according to the present invention includes multiple electrodes, a body impedance measurement unit, a trunk area width detection unit, a body fat mass calculation unit, and a fitting unit. The multiple electrodes are for making contact with predetermined areas of the surface of a measurement subject's body, and include at least back area electrodes for making contact with the surface of a back area that corresponds to an area of the measurement subject's trunk area on the back side thereof. The body impedance measurement unit is a unit that measures a body impedance of the measurement subject's body using the multiple electrodes. The trunk area width detection unit is a unit for measuring a trunk area width and a trunk area depth of the measurement subject. The body fat mass calculation unit is a unit that calculates a body fat mass based on the body impedance measured by the body impedance measurement unit and the trunk area width and trunk area depth detected by the trunk area width detection unit. The fitting unit is a frame-shaped element, capable of being disposed so as to surround the measurement subject's trunk area during a fitted state, for bringing the back area electrodes into contact with the measurement subject's back area surface in a pressurized state. The back area electrodes are provided on a surface of the fitting unit in an exposed state. The trunk area width detection unit is provided in the fitting unit.

In the body fat measurement device according to the present invention, it is preferable for the back area electrodes to be provided on a rear area of the fitting unit so that the surfaces of the back area electrodes that make contact with the back area surface face forward in the fitted state.

In the body fat measurement device according to the present invention, it is preferable for the trunk area width detection unit to be configured of a non-contact range sensor provided on at least one of a right side portion and a left side portion of the fitting unit and a non-contact range sensor provided on a front portion of the fitting unit.

In the body fat measurement device according to the present invention, the configuration may be such that at least one of a right side portion and a left side portion of the fitting unit can be moved along the width direction of the measurement subject's trunk area during the fitted state and at least one of a front portion and a rear portion of the fitting unit can be moved along the depth direction of the measurement subject's trunk area during the fitted state, and in such a case, it is preferable for the trunk area width detection unit to be configured of a movement amount detection sensor that detects the amount by which the portion of the fitting unit that can move has moved.

In the body fat measurement device according to the present invention, both a right side portion and a left side portion of the fitting unit can be moved along the width direction of the measurement subject's trunk area during the fitted state, and both a front portion and a rear portion of the fitting unit can be moved along the depth direction of the measurement subject's trunk area during the fitted state. The trunk area width detection unit is configured of a movement amount detection unit that detects the amount by which the portion of the fitting unit that can move has moved.

In the body fat measurement device according to the present invention, the multiple electrodes further include a pair of flank electrodes for making contact with the surfaces of the measurement subject's flank areas. The fitting unit includes a width direction movement linkage mechanism that links outward movement of the right side portion with outward movement of the left side portion and that links inward movement of the right side portion with inward movement of the left side portion; and a depth direction movement linkage mechanism that links outward movement of the front portion with outward movement of the rear portion and that links inward movement of the front portion with inward movement of the rear portion. The back area electrodes are anchored to the width direction movement linkage mechanism so that the back area electrodes stop at a location midway between the right side portion and the left side portion even when the right side portion and the left side portion are moved outward by the width direction movement linkage mechanism and when the right side portion and the left side portion are moved inward by the width direction movement linkage mechanism. The pair of flank electrodes are anchored to the depth direction movement linkage mechanism so that the flank electrodes stop at a location that is midway between the front portion and the rear portion even when the front portion and the rear portion are moved outward by the depth direction movement linkage mechanism and when the front portion and the rear portion are moved inward by the depth direction movement linkage mechanism.

In the body fat measurement device according to the present invention, the fitting unit further includes a depth-width direction movement linkage mechanism that causes the front portion and the rear portion to be moved outward by the depth direction movement linkage mechanism in tandem with the width direction movement linkage mechanism moving the right side portion and the left side portion outward, and causes the front portion and the rear portion to be moved inward by the depth direction movement linkage mechanism in tandem with the width direction movement linkage mechanism moving the right side portion and the left side portion inward.

In the body fat measurement device according to the present invention, it is preferable for the multiple electrodes to further include upper limb electrodes for making contact with the surfaces of the measurement subject's upper limbs, and for the upper limb electrodes to be provided on the surface of the fitting unit in an exposed state.

In the body fat measurement device according to the present invention, it is preferable for the upper limb electrodes to be provided on at least one of the front portion, the right side portion, and the left side portion that exclude the rear portion of the fitting unit.

It is preferable for the body fat measurement device according to the present invention to further include a unit orientation detection unit for detecting an orientation of the fitting unit. In such a case, it is preferable for the unit orientation detection unit to be configured of an accelerometer provided in the fitting unit.

In the body fat measurement device according to the present invention, it is preferable for a level indicating an orientation of the fitting unit to be provided in the fitting unit.

It is preferable for the body fat measurement device according to the present invention to further include a support column portion that supports the fitting unit so as to be capable of moving along the vertical direction while maintaining the fitting unit in a horizontal orientation.

In the body fat measurement device according to the present invention, it is preferable for the multiple electrodes to further include lower limb electrodes for making contact with the surfaces of the measurement subject's lower limbs. In this case, it is preferable for the body fat measurement device according to the present invention to further include a platform unit for bringing the lower limb electrodes into contact with the soles of the measurement subject's feet when the measurement subject steps onto the platform unit, and in such a case, for the lower limb electrodes to be provided on a top surface of the platform unit in an exposed state. Furthermore, in such a case, it is preferable for the platform unit to include a body weight measurement unit that measures the weight of the measurement subject.

In the body fat measurement device according to the present invention, it is preferable for the multiple electrodes to further include lower limb/hip electrodes for making contact with the surfaces of the measurement subject's lower limbs or hip area. In this case, it is preferable for the fitting unit to include extending unit portions for bringing the lower limb/hip electrodes into contact with the surfaces of the lower limbs or hip area by being pulled out from the fitting unit via connection lines, and in such a case, for the lower limb/hip electrodes to be provided on the surfaces of the extending unit portions in an exposed state.

In the body fat measurement device according to the present invention, it is preferable for the body fat mass calculation unit to include at least one of a visceral fat mass calculation unit that calculates the visceral fat mass of the measurement subject and a subcutaneous fat mass calculation unit that calculates the subcutaneous fat mass of the measurement subject.

Advantageous Effects of Invention

According to the present invention, a body fat measurement device capable of measuring a body fat mass such as a visceral fat mass easily and accurately in a household or the like can be provided.

DESCRIPTION OF EMBODIMENTS

Figure 1A:
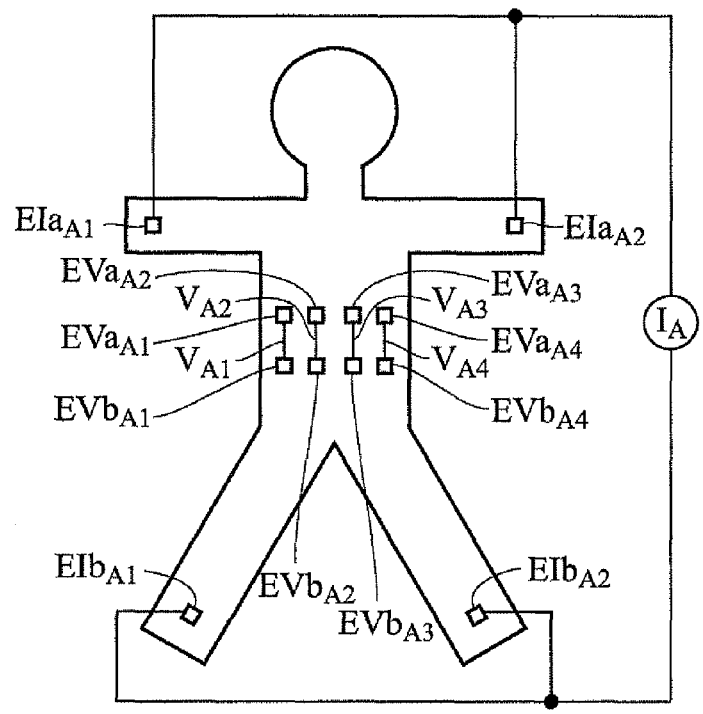
FIGS. 1A and 1B are diagrams illustrating the fundamentals of measurement performed by a body fat measurement device according to a first embodiment of the present invention.

Hereinafter, body fat measurement devices according to respective embodiments of this invention will be described in detail with reference to the drawings. When numbers, amounts, and so on are discussed in the following embodiments, it should be noted that unless explicitly mentioned otherwise, the scope of the present invention is not necessarily limited to those numbers, amounts, and so on. Furthermore, in the case where multiple embodiments are given hereinafter, it is assumed from the outset that the configurations of the respective embodiments can be combined as appropriate unless explicitly mentioned otherwise. In the drawings, identical reference numerals refer to identical or corresponding elements; there are also cases where redundant descriptions are omitted.

Before describing the various embodiments of the present invention, definitions will first be given for terms expressing parts of the body. "Trunk area" refers to the area excluding the head, neck, and four limbs, and corresponds to the trunk of the body. "Back area" refers to the area located on the back side of the stated trunk area, and corresponds to the area of the stated trunk area excluding the abdominal area side and the chest area side. "Back area surface" refers to the entire body surface of the back area, and indicates the surface of the trunk area that can be seen when a measurement subject is observed from the back side. Finally, "body axis" refers to an axis located along the direction in which the trunk area extends, or in other words, an axis extending in a direction approximately perpendicular to a side cross-section of the measurement subject's trunk area.

First Embodiment

Figure 1B:
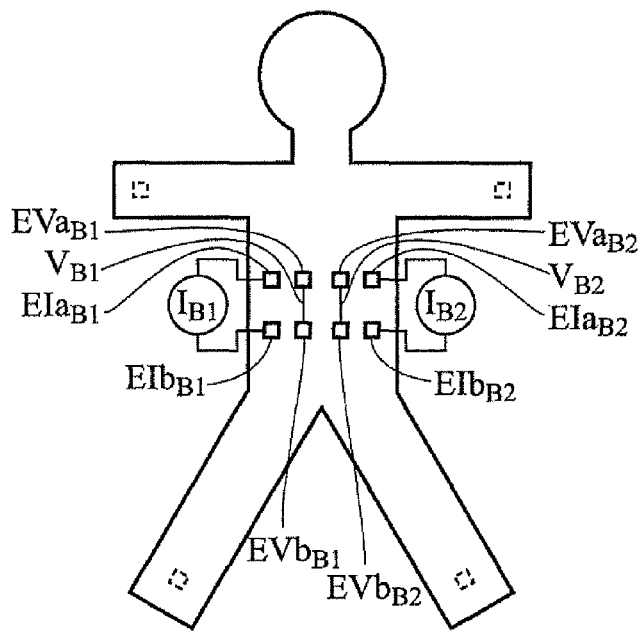

FIGS. 1A and 1B are diagrams illustrating the fundamentals of measurement performed by a body fat measurement device according to a first embodiment of the present invention. Here, FIG. 1A is a diagram illustrating the placement of electrodes when obtaining a body impedance for the entire trunk area, whereas FIG. 1B is a diagram illustrating the placement of electrodes when obtaining a body impedance for a surface layer area on the back area side of the trunk area. First, the fundamentals of measurement performed by the body fat measurement device according to the present embodiment will be described with reference to FIGS. 1A and 1B. Note that FIGS. 1A and 1B both illustrate the measurement subject from the back side thereof.

Fundamentals of Measurement Performed by Body Fat Measurement Device

As shown in FIG. 1A, electrodes $EIa_{A1}$ and $EIa_{A2}$ are attached to the surface of the left hand of the measurement subject and the surface of the right hand of the measurement subject, respectively, in order to obtain the body impedance for the entire trunk area. Likewise, electrodes $EIb_{A1}$ and $EIb_{A2}$ are attached to the surface of the left foot of the measurement subject and the surface of the right foot of the measurement subject, respectively. Four pairs of electrodes are attached to the back area surface of the measurement subject, with each pair disposed so as to follow the body axis direction, and with the four pairs arranged in the widthwise direction of the trunk area. In other words, as shown in FIG. 1A, a total of eight electrodes, or electrodes $EVa_{A1}$, $EVb_{A1}$, $EVa_{A2}$, $EVb_{A2}$, $EVa_{A3}$, $EVb_{A3}$, $EVa_{A4}$, and $EVb_{A4}$, are attached to the back area surface of the measurement subject.

In this state, a constant current $I_A$ that passes through the trunk area is applied to the measurement subject using the electrodes $EIa_{A1}$, $EIa_{A2}$, $EIb_{A1}$, and $EIb_{A2}$ attached to both hands and both feet, respectively. While the constant current $I_A$ is applied, a potential difference $V_{A1}$ is detected using the pair of electrodes $EVa_{A1}$ and $EVb_{A1}$ attached to the back area surface, a potential difference $V_{A2}$ is detected using the pair of electrodes $EVa_{A2}$ and $EVb_{A2}$ attached to the back area surface, a potential difference $V_{A3}$ is detected using the pair of electrodes $EVa_{A3}$ and $EVb_{A3}$ attached to the back area surface, and a potential difference $V_{A4}$ is detected using the pair of electrodes $EVa_{A4}$ and $EVb_{A4}$ attached to the back area surface.

A body impedance Zt of the entire trunk area is calculated from the potential differences $V_{A1}$, $V_{A2}$, $V_{A3}$, and $V_{A4}$ detected in this manner. Note that if the body impedance Zt is found at this time by calculating the average value of the four stated potential differences $V_{A1}$, $V_{A2}$, $V_{A3}$, and $V_{A4}$, it is possible to reduce the influence of variations in the fat distribution within the trunk area.

In this state, the constant current $I_A$ is flowing between both hands and both feet, which are positioned at a distance from the trunk area, and thus almost all of the applied constant current $I_A$ passes through areas of low electrical resistance, or in other words, through areas aside from fat. Accordingly, the stated body impedance Zt calculated from the potential differences $V_{A1}$, $V_{A2}$, $V_{A3}$, and $V_{A4}$ measured using the constant current $I_A$ is greatly influenced by the amount of non-fat areas (internal organs, muscle, and bone) within the trunk area. Accordingly, the area occupied by non-fat areas (called a "non-fat cross-sectional area" hereinafter) Sa in the cross-section of the trunk area in an area corresponding to the location of the navel can be estimated based on the stated body impedance Zt.

Meanwhile, as shown in FIG. 1B, the four pairs of electrodes are attached to the back area surface of the measurement subject with each pair disposed so as to follow the body axis direction, and with the four pairs arranged in the widthwise direction of the trunk area, in order to obtain the body impedance of the surface layer area on the back area side of the trunk area. In other words, as shown in FIG. 1B, a total of eight electrodes, or electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$, are attached to the back area surface of the measurement subject.

In this state, a constant current $I_{B1}$ that passes through the back area locally is applied to the measurement subject using the pair of electrodes $EIa_{A1}$ and $EIb_{B1}$, and a constant current $I_{B2}$ that passes through the back area locally is applied to the measurement subject using the pair of electrodes $EIa_{A1}$ and $EIb_{B2}$. While the constant currents $I_{B1}$ and $I_{B2}$ are applied, a potential difference $V_{B1}$ is detected using the pair of electrodes $EVa_{B1}$ and $EVb_{B1}$ attached to the back area surface, and a potential difference $V_{B2}$ is detected using the pair of electrodes $EVa_{B2}$ and $EVb_{B2}$ attached to the back area surface. Here, the current values of the two constant currents $I_{B1}$ and $I_{B2}$ applied to the measurement subject are set to the same value.

A body impedance Zs of the surface layer area on the back area side of the trunk area is calculated form the potential differences $V_{B1}$ and $V_{B2}$ calculated in this manner. Note that if the body impedance Zs is found at this time by calculating the average value of the two stated potential differences $V_{B1}$ and $V_{B2}$, it is possible to reduce the influence of variations in the fat distribution within the surface layer area in the back area of the trunk area. Note that potential differences can also be calculated in four locations by switching circuits so that the electrodes to which the current was applied serve as electrodes for detecting the potential differences and the electrodes that were detecting the potential differences serve as electrodes for current application. Doing so makes it possible to further reduce the influence of variations in the subcutaneous fat and so on.

In this state, the constant currents $I_{B1}$ and $I_{B2}$ are applied locally to the back area of the trunk area, and thus almost all of both the applied constant currents $I_{B1}$ and $I_{B2}$ pass through the surface layer area of the back area. Accordingly, the stated body impedance Zs calculated from the potential differences $V_{B1}$ and $V_{B2}$ measured using the constant currents $I_{B1}$ and $I_{B2}$ is greatly influenced by the subcutaneous fat mass. Accordingly, the subcutaneous fat cross-sectional area (called a "subcutaneous fat cross-sectional area" hereinafter) Sb in the cross-section of the trunk area including the location of the navel can be estimated based on the stated body impedance Zs.

Next, an example of a computation process for calculating a visceral fat mass using the stated body impedances Zt and Zs obtained in this manner will be described.

If the overall area of the cross-section of the trunk area at the area corresponding to the location of the navel (called a "trunk area cross-sectional area" hereinafter) is taken as St, a visceral fat cross-sectional area Sx can be calculated through the following Formula (1) using the trunk area cross-sectional area St, the non-fat cross-sectional area Sa, and the subcutaneous fat cross-sectional area Sb.

$$Sx = St - Sa - Sb \qquad \text{Formula (1)}$$

Here, the trunk area cross-sectional area St can be calculated using the circumferential length of the trunk area (the so-called waist length), the width of the trunk area, the depth of the trunk area, and so on. For example, in the case where the trunk area cross-sectional area St is to be calculated from the width and depth of the trunk area, assuming that the width of the trunk area is taken as 2a and the depth of the trunk area is taken as 2b, and because the trunk area has a generally oval cross-sectional shape, the trunk area cross-sectional area St can be approximated through the following Formula (2).

$$St = \pi \times a \times b \qquad \text{Formula (2)}$$

However, the trunk area cross-sectional area St approximated through the above Formula (2) is highly likely to contain a significant degree of error, and it is thus preferable to find a more accurate trunk area cross-sectional area St by multiplying that trunk area cross-sectional area St by a coefficient $\alpha$ for reducing error. This coefficient $\alpha$ is obtained, for example, by finding the optimum value for $\alpha$ that fulfills $St' = \alpha \times \pi \times a \times b$, from the relationship between the stated a and b and a trunk area cross-sectional area St' obtained from a sample of a large number of X-ray CT images.

Accordingly, the stated Formula (2) can approximate with a lower degree of error through the following Formula (3) by using the coefficient $\alpha$.

$$St = \alpha \times \pi \times a \times b \qquad \text{Formula (3)}$$

Note that it is preferable to optimize the coefficient $\alpha$ multiplied for correction as described above as appropriate in accordance with information such as the measurement subject's sex, age, height, weight, and so on (hereinafter, this information will be referred to collectively as "measurement subject information"). In other words, the trunk area cross-sectional area St can be approximated with a higher degree of accuracy by changing the value of the stated coefficient $\alpha$ in accordance with the measurement subject information.

As described above, the non-fat cross-sectional area Sa can be calculated based on the body impedance Zt of the entire trunk area. However, the non-fat cross-sectional area Sa cannot be accurately calculated using only the body impedance Zt of the entire trunk area. That is, the non-fat cross-sectional area Sa tends to be proportional to the size of the trunk area, and thus it is necessary to further convert the value obtained from the body impedance Zt in order to calculate the non-fat cross-sectional area Sa. Accordingly, the non-fat cross-sectional area Sa can be expressed through, for example, the following Formula (4).

$$Sa = \beta \times a \times (1/Zt) \qquad \text{Formula (4)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, $\beta$ represents a coefficient for converting the body impedance Zt of the entire trunk area into the non-fat cross-sectional area Sa, and an optimum value can be found, for example, based on a sample of a large number of X-ray CT images, in the same manner as when finding the coefficient $\alpha$. In other words, the optimum value for $\beta$ that fulfils $Sa' = \beta \times a \times (1/Zt)$ can be found from the relationship between a non-fat cross-sectional area Sa' obtained from a sample of a large number of X-ray CT images, the body impedance Zt of the entire trunk area of the measurement subject imaged by the X-ray CT, and the stated a.

Note that it is preferable for the stated coefficient $\beta$ to be optimized as appropriate in accordance with the measurement subject information, in the same manner as the coefficient $\alpha$ mentioned above. In other words, the non-fat cross-sectional area Sa can be approximated with a higher degree of accuracy by changing the value of the stated coefficient $\beta$ in accordance with the measurement subject information.

Furthermore, as described above, the subcutaneous fat cross-sectional area Sb can be calculated based on the body impedance Zs of the surface layer area on the back area side of the trunk area. However, the subcutaneous fat cross-sectional area Sb cannot be accurately calculated using only the body impedance Zs of the surface layer area on the back area side of the trunk area. That is, the subcutaneous fat cross-sectional area Sb tends to be proportional to the size of the trunk area, and thus it is necessary to further convert the value obtained from the body impedance Zs in order to calculate the subcutaneous fat cross-sectional area Sb. Accordingly, the subcutaneous fat cross-sectional area Sb can be expressed through, for example, the following Formula (5).

$$Sb = \gamma \times a \times Zs \qquad \text{Formula (5)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, $\gamma$ represents a coefficient for converting the body impedance Zs of the surface layer area on the back area side of the trunk area into the subcutaneous fat cross-sectional area Sb, and an optimum value can be found, for example, based on a sample of a large number of X-ray CT images, in the same manner as when finding the coefficient $\alpha$ or the coefficient $\beta$. In other words, the optimum value for $\gamma$ that fulfils $Sb' = \gamma \times a \times Zs$ can be found from the relationship between a subcutaneous fat cross-sectional area Sb' obtained from a sample of a large number of X-ray CT images, the body impedance Zs of the surface layer area on the back area side of the trunk area of the measurement subject imaged by the X-ray CT, and the stated a.

Note that it is preferable for the stated coefficient $\gamma$ to be optimized as appropriate in accordance with the measurement subject information, in the same manner as the coefficient $\alpha$ and the coefficient $\beta$ mentioned above. In other words, the subcutaneous fat cross-sectional area Sb can be approximated with a higher degree of accuracy by changing the value of the stated coefficient γ in accordance with the measurement subject information.

As described thus far, in the body fat measurement device according to the present embodiment, the visceral fat cross-sectional area Sx is calculated based on the stated Formula (1) using the trunk area cross-sectional area St, the non-fat cross-sectional area Sa calculated based on the body impedance Zt of the entire trunk area, and the subcutaneous fat cross-sectional area Sb calculated based on the body impedance Zs of the surface layer area on the back area side of the trunk area; more specifically, the visceral fat cross-sectional area Sx is calculated based on the following Formula (6) by substituting the stated Formula (3) through Formula (5) in the stated Formula (1).

$$Sx = \alpha \times \pi \times a \times b - \beta \times a \times (1/Zt) - \gamma \times a \times Zs \quad \text{Formula (6)}$$

Functional Blocks of Body Fat Measurement Device

Figure 2:
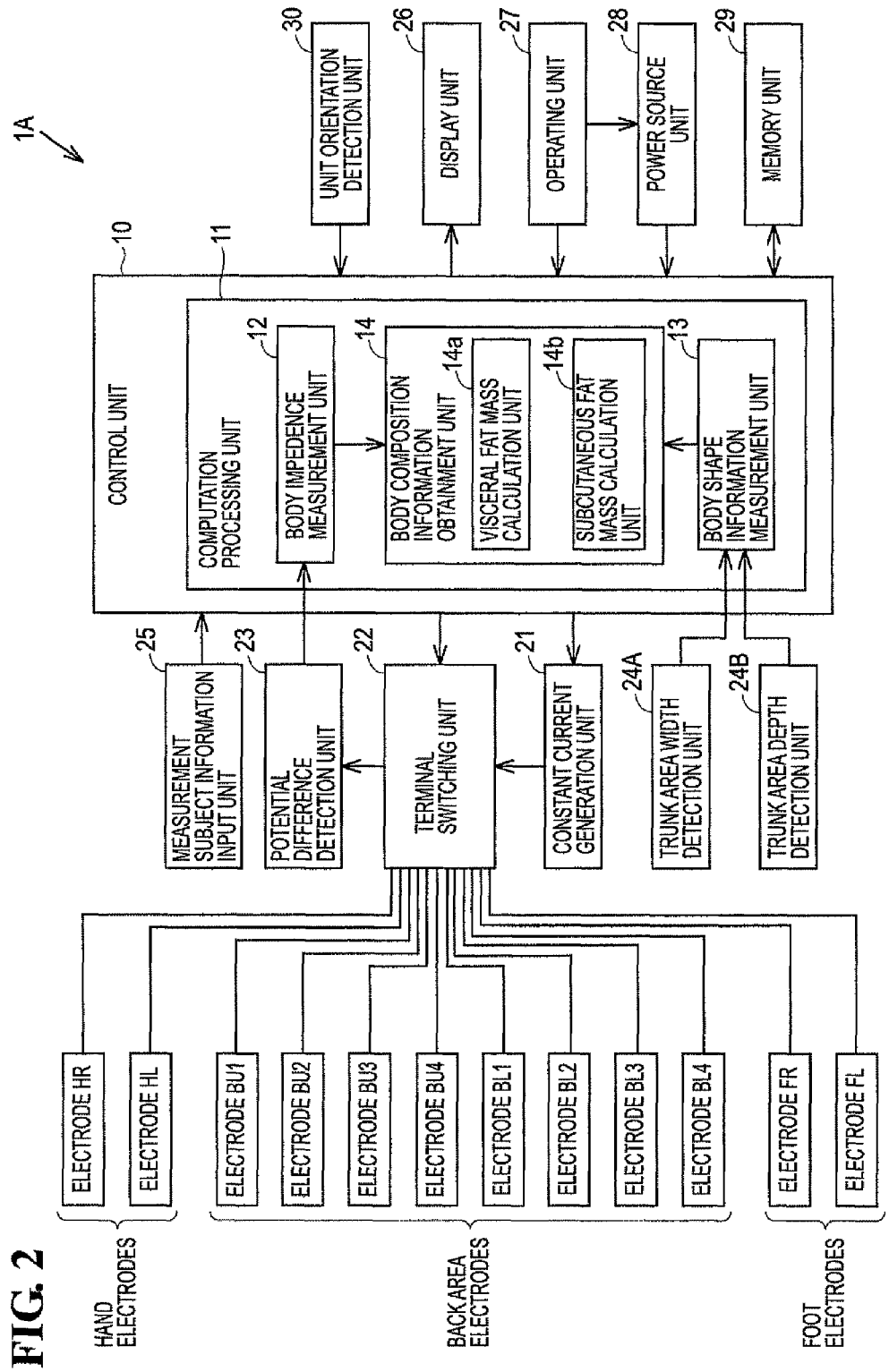
FIG. 2 is a diagram illustrating the functional block configuration of the body fat measurement device according to the first embodiment of the present invention.

FIG. 2 is a diagram illustrating the functional block configuration of the body fat measurement device according to the present embodiment. Next, the functional block configuration of the body fat measurement device according to the present embodiment will be described with reference to FIG. 2.

As shown in FIG. 2, a body fat measurement device 1A according to the present embodiment primarily includes: a control unit 10; a constant current generation unit 21; a terminal switching unit 22; a potential difference detection unit 23; a trunk area width detection unit 24A; a trunk area depth detection unit 24B; a measurement subject information input unit 25; a display unit 26; an operating unit 27; a power source unit 28; a memory unit 29; a unit orientation detection unit 30; and multiple electrodes HR, HL, BU1-BU4, BL1-BL4, FR, and FL that are fitted to the body of the measurement subject. The control unit 10 includes a computation processing unit 11, and the computation processing unit 11 has a body impedance measurement unit 12, a body shape information measurement unit 13, and a body composition information obtainment unit 14.

The control unit 10 is configured of, for example, a CPU (Central Processor Unit), and is a unit for controlling the body fat measurement device 1A as a whole. Specifically, the control unit 10 outputs instructions to the various aforementioned functional blocks, accepts inputs of various types of information from the various aforementioned functional blocks, performs various types of computation processes based on the various types of information accepted, and so on. The various types of computation processes are carried out by the stated computation processing unit 11 provided in the control unit 10.

The aforementioned multiple electrodes include: hand electrodes HR and HL serving as upper limb electrodes placed in contact with surfaces of the upper limbs of the measurement subject; back area electrodes BU1-BU4 and BL1-BL4 placed in contact with the back area surface of the measurement subject; and foot electrodes FR and FL serving as lower limb electrodes placed in contact with surfaces of the lower limbs of the measurement subject. Of these, the hand electrodes HR and HL are placed in contact with the measurement subject's palms, whereas the foot electrodes FR and FL are placed in contact with the soles of the measurement subject's feet.

Meanwhile, as shown in FIGS. 1A and 1B, the back area electrodes BU1-BU4 and BL1-BL4 are arranged in rows and placed in contact with the back area surface of the measurement subject. Note that the hand electrodes HR and HL, back area electrodes BU1-BU4 and BL1-BL4, and foot electrodes FR and FL are all electrically connected to the aforementioned terminal switching unit 22.

The terminal switching unit 22 is configured of, for example, a relay circuit; based on instructions inputted from the control unit 10, the terminal switching unit 22 electrically connects specific electrodes selected from the stated multiple electrodes to the constant current generation unit 21 and electrically connects specific electrodes selected from the stated multiple electrodes to the potential difference detection unit 23. Through this, the electrodes electrically connected to the constant current generation unit 21 by the terminal switching unit 22 function as constant current application electrodes, and the electrodes electrically connected to the potential difference detection unit 23 by the terminal switching unit 22 function as potential difference detection electrodes. In other words, by the terminal switching unit 22 operating based on instructions inputted from the control unit 10, the respective multiple electrodes HR, HL, BU1-BU4, BL1-BL4, FR, and FL function as the respective electrodes $EIa_{A1}$, $EIa_{A2}$, $EIb_{A1}$, $EIb_{A2}$, $EVa_{A1}$, $EVb_{A1}$, $EVa_{A2}$, $EVb_{A2}$, $EVa_{A3}$, $EVb_{A3}$, $EVa_{A4}$, and $EVb_{A4}$ shown in FIG. 1A and the respective electrodes $EIa_{A1}$, $EIb_{B1}$, $EVa_{B1}$, $EVb_{B1}$, $EVa_{B2}$, $EVb_{B2}$, $EIa_{B2}$, and $EIb_{B2}$ shown in FIG. 1B.

The constant current generation unit 21 generates a constant current based on an instruction inputted from the control unit 10, and supplies the generated constant current to the stated constant current application electrodes via the terminal switching unit 22. A high-frequency current (for example, 50 kHz, 500 μA) that can be used effectively for measuring body composition information is selected as the constant current generated by the constant current generation unit 21. Through this, the constant current can be applied to the measurement subject via the constant current application electrodes.

The potential difference detection unit 23 detects a potential difference between the electrodes electrically connected to the potential difference detection unit 23 by the terminal switching unit 22 (that is, the potential difference detection electrodes), and outputs the detected potential difference to the control unit 10. Through this, the potential difference between the potential difference detection electrodes is detected in a state in which the aforementioned constant current is applied to the measurement subject.

The trunk area width detection unit 24A is a detection unit for measuring the width of the measurement subject's trunk area without making contact therewith, and is configured of, for example, a range sensor such as an optical sensor. Meanwhile, the trunk area depth detection unit 24B is a detection unit for measuring the depth of the measurement subject's trunk area without making contact therewith, and is configured of, for example, a range sensor such as an optical sensor. The trunk area width detection unit 24A and the trunk area depth detection unit 24B output signals based on the values detected to the body shape information measurement unit 13. In addition to the stated optical sensors, it should be noted that various types of non-contact range sensors that use ultrasound waves or electromagnetic waves (light of various wavelength ranges including laser light, visible light, and so on, radio waves, magnetism, electrical fields, and the like) can also be used as the trunk area width detection unit 24A and the trunk area depth detection unit 24B.

The measurement subject information input unit 25 is a unit for obtaining information regarding the measurement subject used in computation processes carried out by the computation processing unit 11, and is configured of, for example, keys and the like that can be depressed by the measurement subject. Here, the measurement subject information includes at least one of the sex, age, height, weight, and so on of the measurement subject, as mentioned above. The measurement subject information input unit 25 accepts the input of measurement subject information, and outputs the accepted measurement subject information to the control unit 10. Note that the measurement subject information input unit 25 is not absolutely necessary in the configuration of the present invention, and whether or not to provide the measurement subject information input unit 25 can be determined based on whether or not it is necessary to use the measurement subject information in the computation processes performed by the computation processing unit 11.

The unit orientation detection unit 30 is a detection element for detecting the orientation of a fitting unit 100A (mentioned later; see FIGS. 3 through 10), and is configured of, for example, an accelerometer. The unit orientation detection unit 30 outputs a signal based on a detection value to the control unit 10.

The computation processing unit 11 includes the body impedance measurement unit 12, the body shape information measurement unit 13, and the body composition information obtainment unit 14, as mentioned above. Meanwhile, the body composition information obtainment unit 14 includes a visceral fat mass calculation unit 14a and a subcutaneous fat mass calculation unit 14b. The body impedance measurement unit 12 calculates the body impedance based on a signal inputted from the potential difference detection unit 23, and outputs that body impedance to the body composition information obtainment unit 14. The body shape information measurement unit 13 calculates the width and the depth of the measurement subject's trunk area based on the signals inputted from the trunk area width detection unit 24A and the trunk area depth detection unit 24B, and outputs the calculated information to the body composition information obtainment unit 14. The body composition information obtainment unit 14 calculates and obtains the body composition information based on the body impedance inputted from the body impedance measurement unit 12, the width and depth of the trunk area inputted from the body shape information measurement unit 13, and in some cases, the measurement subject information inputted from the measurement subject information input unit 25 as well. More specifically, the visceral fat mass calculation unit 14a calculates a visceral fat mass and the subcutaneous fat mass calculation unit 14b calculates a subcutaneous fat mass.

The display unit 26 is configured of, for example, an LCD (Liquid Crystal Display) or the like, and displays the body composition information calculated by the body composition information obtainment unit 14 as mentioned above. More specifically, the visceral fat mass calculated by the visceral fat mass calculation unit 14a and the subcutaneous fat mass calculated by the subcutaneous fat mass calculation unit 14b are displayed in the display unit 26 based on signals outputted from the control unit 10. Here, with the body fat measurement device 1A according to the present embodiment, the visceral fat mass is displayed as, for example, the visceral fat cross-sectional area, and the subcutaneous fat mass is displayed as, for example, the subcutaneous fat cross-sectional area.

The display unit 26 also has a function for displaying the orientation of the fitting unit 100A detected by the stated unit orientation detection unit 30. More specifically, based on a signal outputted from the control unit 10, the display unit 26 visualizes and displays the orientation of the fitting unit 100A detected by the stated unit orientation detection unit 30.

The operating unit 27 is a unit through which the measurement subject inputs commands to the body fat measurement device 1A, and is configured of, for example, buttons and the like that can be depressed by the measurement subject. Note that the operating unit 27 includes various types of operation buttons such as a power button, a measure button, and so on.

The power source unit 28 is a unit for supplying electrical power to the control unit 10, and uses an internal power source such as a battery, an external power source such as an AC outlet, or the like.

The memory unit 29 is configured of, for example, a random access memory (RAM) or a read-only memory (ROM), and is a unit for storing various types of data, programs, and the like for the body fat measurement device 1A. The memory unit 29 stores, for example, the aforementioned measurement subject information, the calculated body composition information, a body composition information measurement program for executing a body composition information measurement process (mentioned later), and so on.

Body Fat Measurement Device 1A

Figure 3:
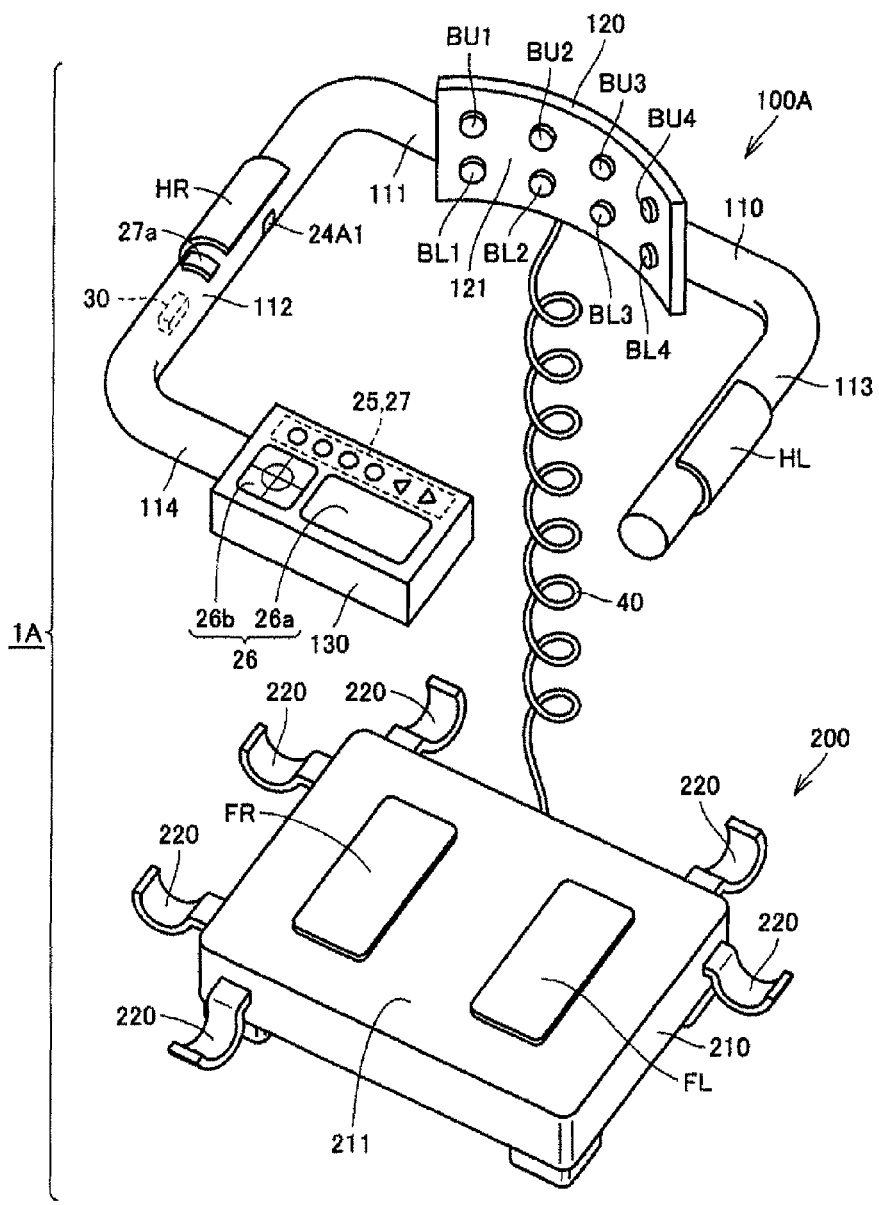
FIG. 3 is a perspective view illustrating the body fat measurement device according to the first embodiment of the present invention in an unstored state.
Figure 4:
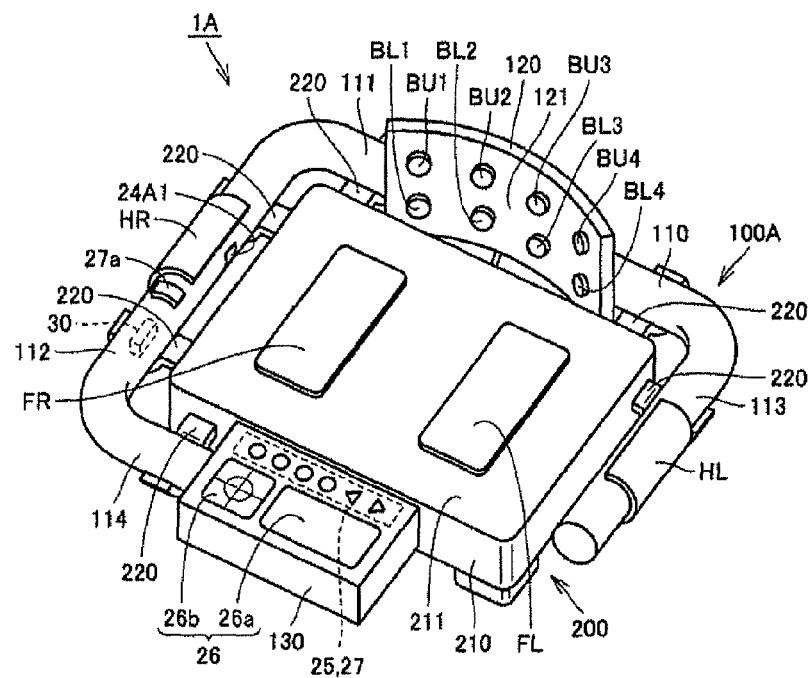
FIG. 4 is a perspective view illustrating the body fat measurement device according to the first embodiment of the present invention in a stored state.
Figure 5:
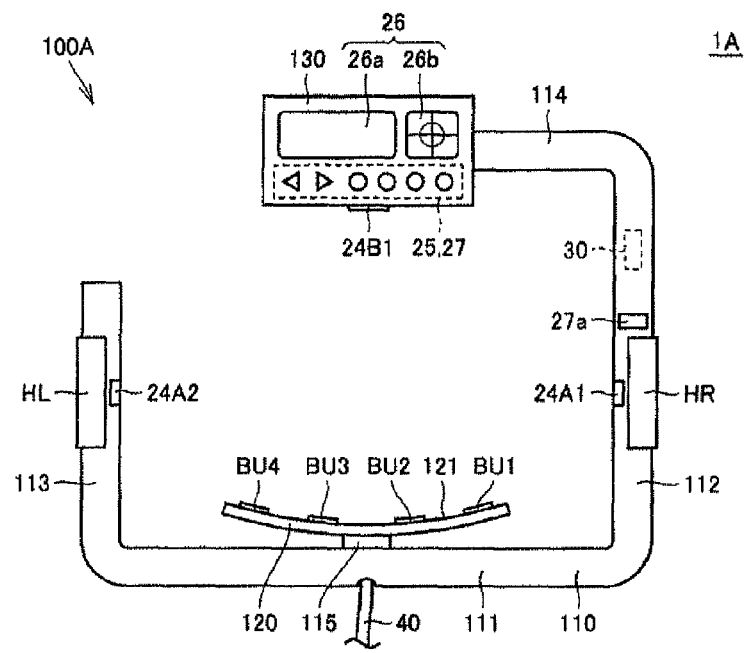
FIG. 5 is a top view of a fitting unit of the body fat measurement device according to the first embodiment of the present invention.

FIG. 3 is a perspective view illustrating the body fat measurement device according to the present embodiment in an unstored state, whereas FIG. 4 is a perspective view illustrating the body fat measurement device in a stored state. FIG. 5, meanwhile, is a top view of a fitting unit shown in FIGS. 3 and 4. Next, the structure of the body fat measurement device according to the present embodiment will be described in detail with reference to FIGS. 3 through 5.

As shown in FIGS. 3 and 4, the body fat measurement device 1A according to the present embodiment includes the fitting unit 100A and a platform unit 200. The fitting unit 100A has a frame shape capable of being disposed so as to surround the trunk area of the measurement subject in a fitted state, which will be described later. Meanwhile, the platform unit 200 is shaped as a platform onto which the measurement subject can step. Note that the fitting unit 100A and the platform unit 200 are connected by a connection cable 40 that electrically connects electrical circuitry provided therein.

As shown in FIGS. 3 through 5, the fitting unit 100A includes: a frame member 110 that includes a rod-shaped rear frame portion 111, a rod-shaped right-side frame portion 112, a rod-shaped left-side frame portion 113, and a rod-shaped front frame portion 114; an electrode support member 120 attached to the rear frame portion 111 of the frame member 110; and a display unit portion 130 attached to the front frame portion 114 of the frame member 110.

The frame member 110 has a frame-shaped outer shape that is approximately rectangular when viewed from above, and has a hollow opening area into which the measurement subject can enter (in other words, into which the measurement subject can insert his/her trunk area). The hollow opening area is defined by the stated rear frame portion 111, right-side frame portion 112, left-side frame portion 113, and front frame portion 114. Note that the left-side frame portion 113 and the front frame portion 114 are not connected, and the aforementioned display unit portion 130 is attached to the end of the front frame portion 114 that is adjacent to the unconnected area.

The electrode support member 120 is disposed in approximately the center of the rear frame portion 111 of the frame member 110 so as to protrude inward. The electrode support member 120 is configured of a curved plate that is bent so that both ends thereof are positioned forward and the center thereof is positioned rearward. The aforementioned back area electrodes BU1-BU4 and BL1-BL4 are provided so as to be exposed on a front surface 121 of the electrode support member 120, and preferably, the back area electrodes BU1-BU4 and BL1-BL4 protrude slightly from the front surface 121 of the electrode support member 120. Here, the electrode support member 120 is positioned and attached on the front surface of the rear frame portion 111 so that surfaces of the back area electrodes BU1-BU4 and BL1-BL4 that make contact with the back area surface of the measurement subject face forward during the fitted state, which will be mentioned later.

Meanwhile, as shown in FIG. 5, the electrode support member 120 is attached to the rear frame portion 111 of the frame member 110 via a connection portion 115 including, for example, a ball joint. Through this, the electrode support member 120 is supported by the rear frame portion 111 so as to be capable of swinging. Note that it is preferable for the direction of the swinging to be limited so that the electrode support member 120 can swing only to the left and right in the horizontal plane. Employing such a configuration makes it possible to bring the back area electrodes BU1-BU4 and BL1-BL4 provided on the front surface 121 of the electrode support member 120 into contact with the back area of the measurement subject with certainty and with an appropriate pressure during the fitted state, which will be mentioned later.

Alternatively, the connection portion 115 may be provided with an elastic member such as a spring, and configured so that the electrode support member 120 is elastically supported on the rear frame portion 111. Employing such a configuration makes it possible to bring the back area electrodes BU1-BU4 and BL1-BL4 provided on the front surface 121 of the electrode support member 120 into contact with the back area of the measurement subject with more certainty and with a more appropriate pressure during the fitted state, which will be mentioned later.

As shown in FIGS. 3 through 5, the aforementioned hand electrode HR is provided in approximately the center of the right-side frame portion 112 of the frame member 110. The hand electrode HR is positioned so as to be exposed on the surface of the right-side frame portion 112 of the frame member 110. Meanwhile, the area of the right-side frame portion 112 of the frame member 110 in which the hand electrode HR is provided is formed in a rod shape, so as to be capable of being gripped by the measurement subject's right hand. Here, it is preferable for the surface of the hand electrode HR that makes contact with the palm of the measurement subject's right hand to be disposed so as to mainly face outward from the frame member 110.

Meanwhile, an optical sensor, serving as the aforementioned trunk area width detection unit 24A, is embedded inside approximately the center of the right-side frame portion 112 of the frame member 110, and a detection window portion 24A1 is provided on the inner side of the right-side frame portion 112 in the area in which the optical sensor is embedded. The detection window portion 24A1 is configured of a member that allows light emitted from the optical sensor to pass through.

In addition, an accelerometer serving as the aforementioned unit orientation detection unit 30 is embedded within an area near the front end of the right-side frame portion 112 of the frame member 110. The accelerometer is positioned relative to the frame member 110 so as to be capable of detecting whether a plane including an axis line of the frame member 110 (in other words, a plane orthogonal to an axis line of the hollow opening area defined by the frame member 110) is parallel to a horizontal plane, or to what degree the plane is angled relative to the horizontal plane; the configuration is such that multiple accelerometers are combined, if necessary.

Furthermore, a measure button 27a is provided in a predetermined location of the right-side frame portion 112 of the frame member 110. Preferably, the measure button 27a is provided in a location adjacent to the hand electrode HR. As a result, it is not necessary for the measurement subject to move his/her right hand during measurement, which makes it possible to provide superior operability.

The aforementioned hand electrode HL is provided in approximately the center of the left-side frame portion 113 of the frame member 110. The hand electrode HL is positioned so as to be exposed on the surface of the left-side frame portion 113 of the frame member 110. Meanwhile, the area of the left-side frame portion 113 of the frame member 110 in which the hand electrode HL is provided is formed in a rod shape, so as to be capable of being gripped by the measurement subject's left hand. Here, it is preferable for the surface of the hand electrode HL that makes contact with the palm of the measurement subject's left hand to be disposed so as to mainly face outward from the frame member 110.

Meanwhile, as shown in FIG. 5, an optical sensor, serving as the aforementioned trunk area width detection unit 24A, is embedded inside approximately the center of the left-side frame portion 113 of the frame member 110, and a detection window portion 24A2 is provided on the inner side of the left-side frame portion 113 in the area in which the optical sensor is embedded. The detection window portion 24A2 is configured of a member that allows light emitted from the optical sensor to pass through.

As shown in FIGS. 3 through 5, the aforementioned display unit portion 130 is attached to the front frame portion 114 of the frame member 110. The display unit 26 is provided in the top surface of the display unit portion 130. Here, the display unit 26 includes a first display unit 26a for displaying measurement results, various types of guides, and so on as numbers, text, or graphs, and a second display unit 26b for visualizing and displaying the orientation of the fitting unit 100A. Meanwhile, the measurement subject information input unit 25 and the operating unit 27, excluding the measure button 27a, are provided on an area of the top surface of the display unit portion 130 that is adjacent to the display unit 26. Note that it is preferable for the display unit portion 130 to be located in front of the measurement subject during the fitted state, and for this reason, the display unit portion 130 is disposed forward from the aforementioned electrode support member 120 (that is, in approximately the center of the horizontal direction of the frame member 110).

Meanwhile, as shown in FIG. 5, an optical sensor, serving as the aforementioned trunk area depth detection unit 24B, is embedded inside the display unit portion 130, and a detection window portion 24B1 is provided on the rear surface side of the display unit portion 130 in the area in which the optical sensor is embedded. The detection window portion 24B1 is configured of a member that allows light emitted from the optical sensor to pass through.

Meanwhile, as shown in FIGS. 3 and 4, the platform unit 200 includes a box-shaped platform portion 210, and support portions 220 that protrude outward from predetermined locations on the front surface, the rear surface, the right-side surface, and the left-side surface of the platform portion 210.

The platform portion 210 has a top surface 211 onto which the measurement subject steps, and the aforementioned foot electrodes FR and FL are respectively provided in predetermined locations of the top surface 211. The foot electrodes FR and FL are positioned so as to be exposed on the top surface of the platform portion 210. Here, the configuration is such that the contact surfaces of the foot electrodes FR and FL that make contact with the sole of the measurement subject's right foot and the sole of the measurement subject's left foot are both facing upward.

As shown in FIG. 4, the support portions 220 are units for supporting and storing the fitting unit 100A during the stored state, and have shapes that are capable of accepting and supporting the rear frame portion 111, the right-side frame portion 112, the left-side frame portion 113, and the front frame portion 114, respectively, of the frame member 110. As shown in FIG. 4, during the stored state, the frame member 110 of the fitting unit 100A is placed so as to surround the platform portion 210 of the platform unit 200. Note that in the stored state, it is preferable for the configuration to be such that the connection cable 40 that connects the fitting unit 100A to the platform unit 200 is contained within the platform unit 200. To achieve such a configuration, a reel member capable of taking up the connection cable 40 into the interior of the platform unit 200 may be provided.

The aforementioned control unit 10, constant current generation unit 21, terminal switching unit 22, potential difference detection unit 23, memory unit 29, and so on shown in FIG. 2 may be provided within the fitting unit 100A, or may be provided within the platform portion 210. Furthermore, although the measurement subject information input unit 25, the display unit 26, and operating unit 27 are provided in the fitting unit 100A of the body fat measurement device 1A according to the present embodiment, those units may be provided within the platform unit 200.

Measurement Procedure to be Followed by Measurement Subject

Figure 6:
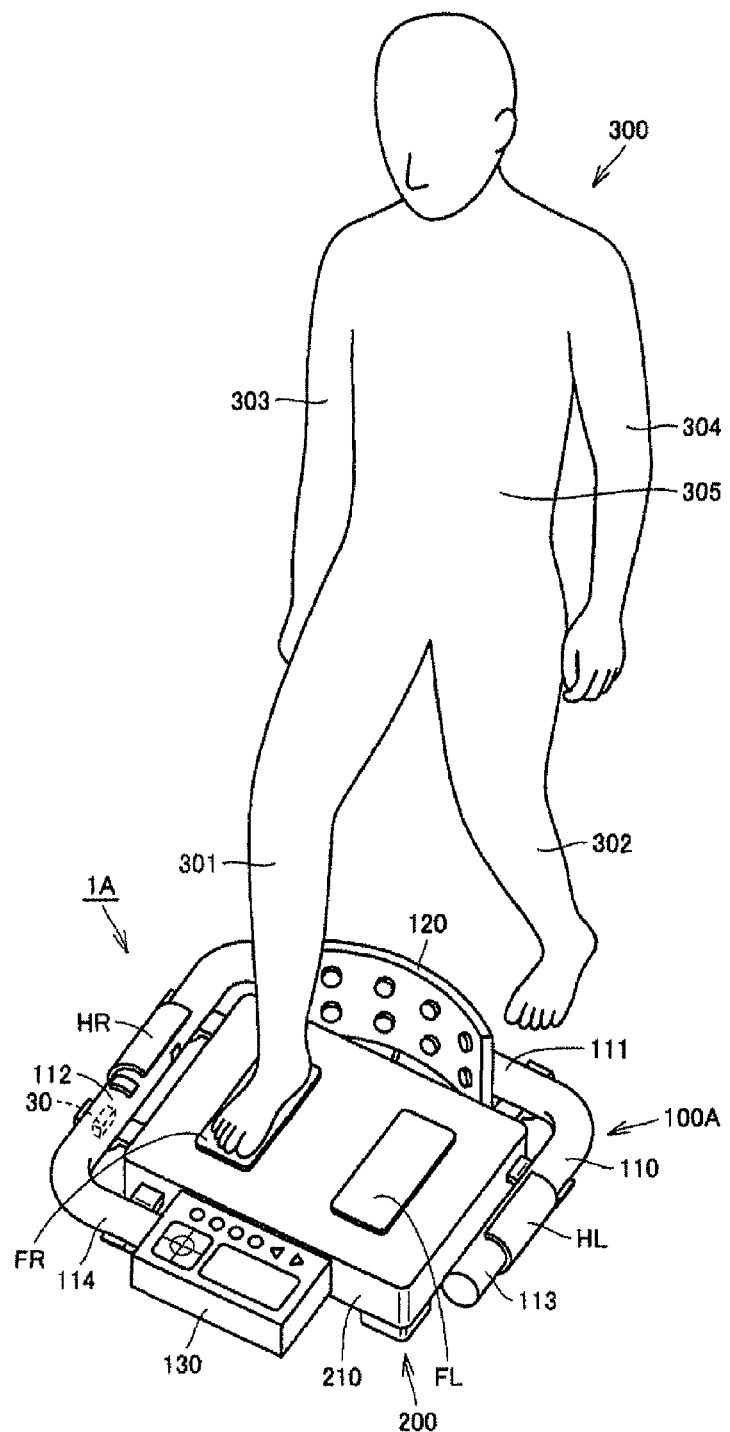
FIG. 6 is a diagram illustrating a measurement procedure to be performed by a measurement subject when carrying out a measurement using the body fat measurement device according to the first embodiment of the present invention.
Figure 7:
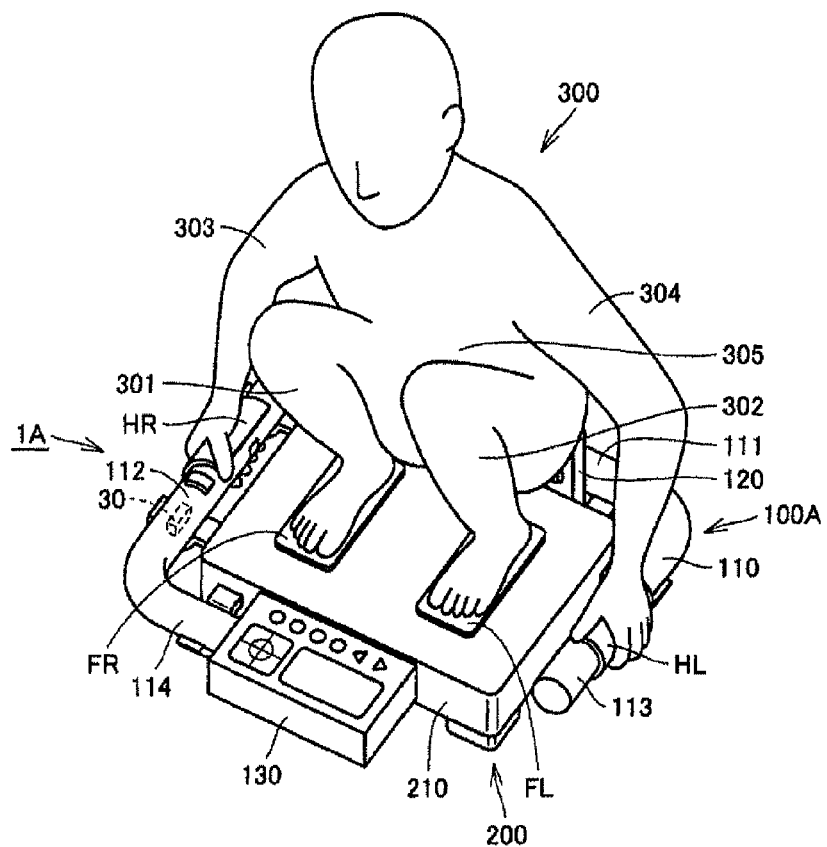
FIG. 7 is a diagram illustrating a measurement procedure to be performed by a measurement subject when carrying out a measurement using the body fat measurement device according to the first embodiment of the present invention.
Figure 8:
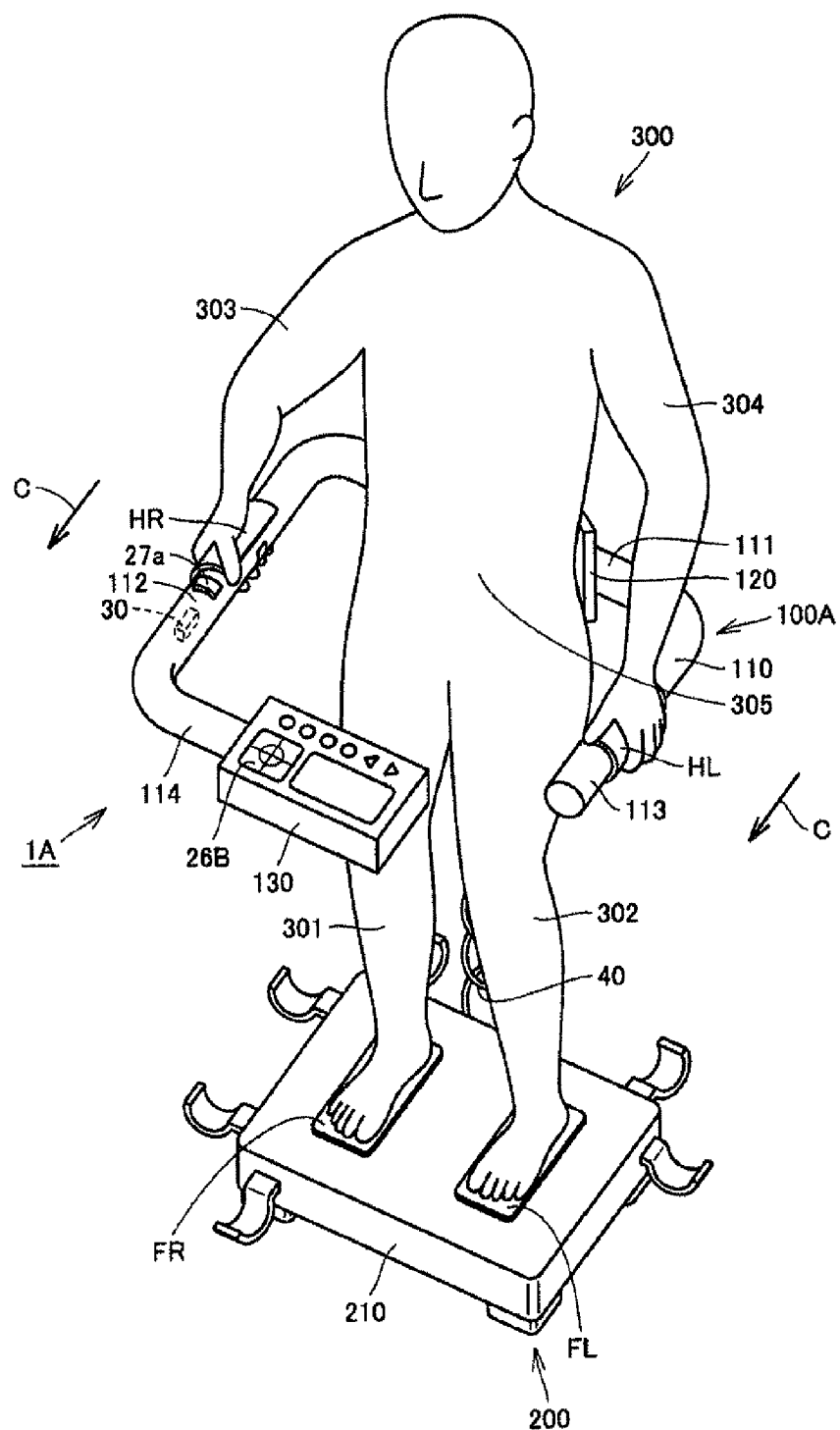
FIG. 8 is a diagram illustrating a measurement procedure to be performed by a measurement subject when carrying out a measurement using the body fat measurement device according to the first embodiment of the present invention.
Figure 9:
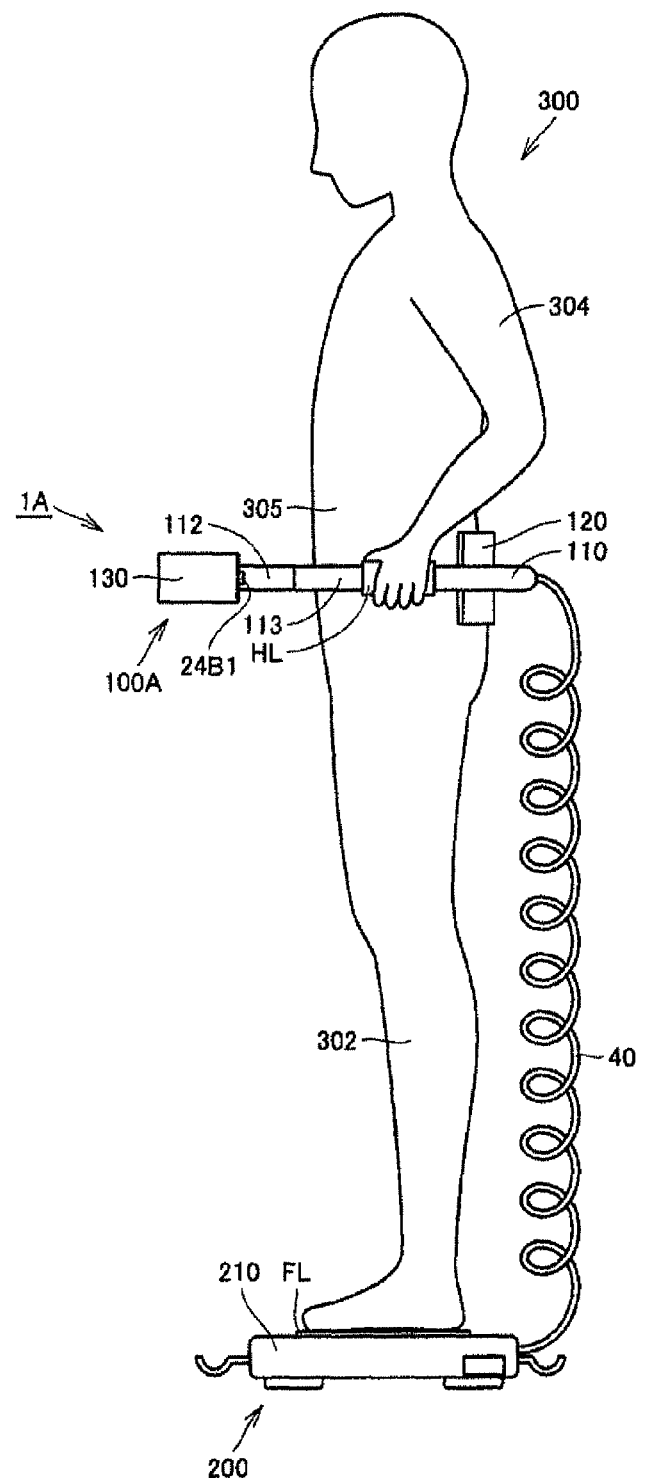
FIG. 9 is a diagram illustrating a fitted state of the fitting unit of the body fat measurement device according to the first embodiment of the present invention.
Figure 10:
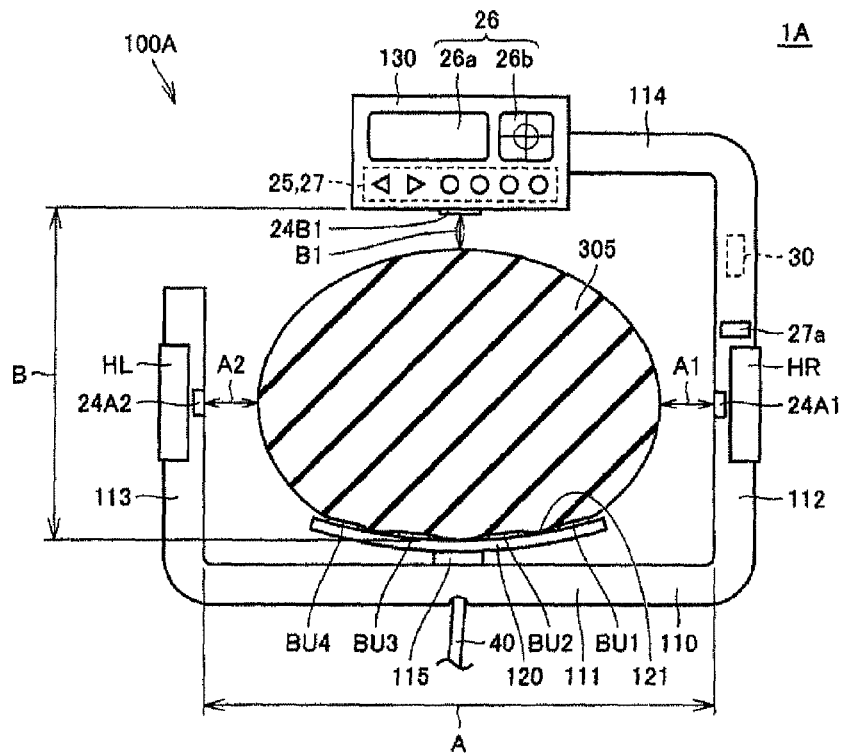
FIG. 10 is a diagram illustrating a fitted state of the fitting unit of the body fat measurement device according to the first embodiment of the present invention.

FIGS. 6 through 8 are diagrams illustrating a measurement procedure to be performed by a measurement subject when carrying out a measurement using the body fat measurement device according to the present embodiment. Meanwhile, FIGS. 9 and 10 are diagrams illustrating the fitting unit of the body fat measurement device according to the present embodiment in the fitted state. Next, a measurement procedure to be performed by the measurement subject and the fitted state of the fitting unit when carrying out measurement using the body fat measurement device according to the present embodiment will be described with reference to FIGS. 6 through 10.

As shown in FIG. 6, when measuring body fat mass using the body fat measurement device 1A according to the present embodiment, first, a measurement subject 300 steps onto the platform unit 200 of the body fat measurement device 1A in the stored state. At this time, the measurement subject 300 brings the sole of his/her right foot 301 into contact with the foot electrode FR provided on the platform unit 200, and brings the sole of his/her left foot 302 into contact with the foot electrode FL provided on the platform unit 200.

Next, as shown in FIG. 7, the measurement subject 300 bends his/her upper body and assumes a squatting position, and grips the right-side frame portion 112 of the fitting unit 100A with his/her right hand 303 and the left-side frame portion 113 of the fitting unit 100A with his/her left hand 304. At this time, the measurement subject 300 brings the palm of his/her right hand 303 into contact with the hand electrode HR provided in the fitting unit 100A, and brings the palm of his/her left hand 304 into contact with the hand electrode HL provided in the fitting unit 100A.

Next, as shown in FIG. 8, the measurement subject 300 straightens his/her upper body while gripping the fitting unit 100A, and assumes a standing position. As this time, the measurement subject 300 does not change his/her foot placement, keeping the sole of his/her right foot 301 in contact with the foot electrode FR and the sole of his/her left foot 302 in contact with the foot electrode FL. Here, the measurement subject 300 lifts the fitting unit 100A by straightening his/her body, and the trunk area 305 of the measurement subject 300 is then positioned in the hollow opening area of the fitting unit 100A, surrounded by the frame member 110. Note that the connection cable 40 is pulled from the platform unit 200 when the fitting unit 100A is lifted.

Next, the measurement subject 300 adjusts the position of the fitting unit 100A by moving the fitting unit 100A in the direction of an arrow C in FIG. 8 while continuing to grip the fitting unit 100A, so that the front surface 121 of the electrode support member 120 provided in the fitting unit 100A is pressed against the back area surface (more specifically, against the surface of his/her hips on the back side).

At this time, the measurement subject 300 adjusts the pressure of the electrode support member 120 against his/her back area surface, and, while viewing and referring to the second display unit 26b that displays the orientation of the fitting unit 100A in a visible state, adjusts the orientation of the fitting unit 100A so that the fitting unit 100A is positioned horizontally. To be more specific, the measurement subject 300 positions the fitting unit 100A horizontally by adjusting the angles of the right hand and left hand that grip the right-side frame portion 112 and left-side frame portion 113 of the frame member 110, adjusting the spatial positions where the right hand and left hand are placed, and so on. The measurement subject 300 maintains the horizontal orientation after adjusting the orientation of the fitting unit 100A.

As a result, the fitting unit 100A enters the fitted state shown in FIGS. 9 and 10, and the measurement of body fat mass can be started. Here, in order to start the measurement of the body fat mass, the measurement subject 300 may depress the measure button 27a using the thumb of his/her right hand 303. Although descriptions have been omitted above, the measurement subject 300 is required to press the power button at an appropriate timing. Although the timing at which the power button is pressed is not particularly limited, it is preferable for the power button to be pressed before the measurement subject 300 assumes a squatting position and grips the fitting unit 100A.

As shown in FIGS. 9 and 10, in the fitted state, where the fitting unit 100A is fitted to the measurement subject 300, the optical sensors serving as the trunk area width detection unit 24A and the optical sensor serving as the trunk area depth detection unit 24B are positioned around the trunk area 305 in a position including the location of the navel of the measurement subject 300. Accordingly, the light emitted from the pair of optical sensors serving as the trunk area width detection unit 24A can irradiate the right side surface of the trunk area 305 of the measurement subject 300 (in other words, the surface of the right flank) and the left side surface of the trunk area 305 (in other words, the surface of the left flank) through the detection window portions 24A1 and 24A2, and the light emitted from the optical sensor serving as the trunk area depth detection unit 24B can irradiate the front surface of the trunk area 305 of the measurement subject 300 (in other words, the vicinity of the location of the navel in the abdominal area) through the detection window portion 24B1.

At this time, it is important for the fitting unit 100A to be kept in a horizontal orientation in order to accurately measure the trunk area width and trunk area depth using the optical sensors. Accordingly, in the body fat measurement device 1A according to the present embodiment, the aforementioned unit orientation detection unit 30 is provided in the fitting unit 100A, and the orientation of the fitting unit 100A as detected by the unit orientation detection unit 30 is displayed in a visible manner in the second display unit 26b. In other words, the measurement subject 300 can be guided by viewing the second display unit 23b and using the second display unit 23b as a reference for maintaining the orientation of the fitting unit 100A in a horizontal orientation.

Here, as shown in FIG. 10, a width 2a of the trunk area 305 of the measurement subject 300 can be calculated using a distance A1 (that is, the distance between the right-side frame portion 112 and the right side surface of the trunk area 305 of the measurement subject 300) and a distance A2 (that is, the distance between the left-side frame portion 113 and the left side surface of the trunk area 305 of the measurement subject 300) detected by the pair of optical sensors serving as the trunk area width detection unit 24A, along with a predetermined distance A (that is, the distance between the right-side frame portion 112 and the left-side frame portion 113). Likewise, a depth 2b of the trunk area 305 of the measurement subject 300 can be calculated using a distance B1 detected by the optical sensor serving as the trunk area depth detection unit 24B (that is, the distance between the rear surface of the display unit portion 130 and the front surface of the trunk area 305 of the measurement subject 300) and a predetermined distance B (that is, the distance between the rear surface of the display unit portion 130 and the center of the front surface 121 of the electrode support member 120 in the horizontal direction).

Assuming that the orientation of the fitting unit 100A is not being maintained in a horizontal orientation, the fitting unit 100A will tilt, causing the stated distance B1, distance B2, and distance A1 to be incorrectly measured, which in turn leads to problems such as the trunk area width and trunk area depth measurements containing errors or that the trunk area width and trunk area depth cannot be measured at all; however, employing the aforementioned configuration eliminates these problems.

Figure 11:
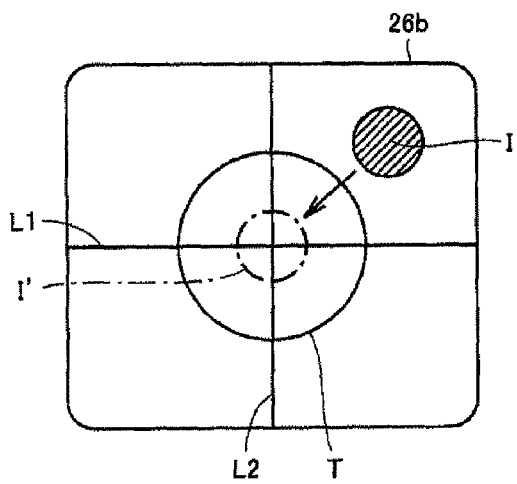
FIG. 11 is a diagram illustrating an example of a display in a second display unit that displays an orientation of the fitting unit of the body fat measurement device according to the first embodiment of the present invention.

FIG. 11 is a diagram illustrating an example of a display in the second display unit that displays the orientation of the fitting unit of the body fat measurement device according to the present embodiment. Next, an example of the display in the second display unit that displays the orientation of the fitting unit of the body fat measurement device according to the present embodiment will be described with reference to FIG. 11.

As shown in FIG. 11, with the body fat measurement device 1A according to the present embodiment, a screen is configured so that the measurement subject can instinctively recognize the orientation of the fitting unit 100A. To be more specific, a guide line L1 that represents the horizontal direction of the fitting unit 100A and a guide line L2 that represents the depth direction of the fitting unit 100A are indicated in the display screen of the second display unit 26b, and furthermore, a region T expressing a permissible range of the orientation of the fitting unit 100A is indicated, in an ancillary manner, as a circle in the center of which the guide line L1 and the guide line L2 intersect. An indicator I, expressing the result of the detection performed by the unit orientation detection unit 30, a shown in the screen as, for example, a circle.

Here, the display state shown in FIG. 11 indicates that a right-front area of the fitting unit 100A (that is, the area of connection between the right-side frame portion 112 and the front frame portion 114) is lower than the other areas, and thus the measurement subject adjusts the orientation of the fitting unit 100A so that the indicator I falls within the aforementioned region T that expresses the permissible range (that is, so that the indicator I moves to the position indicated by I', shown as a broken circle in FIG. 11).

Processing Flow of Control Unit of Body Fat Measurement Device

Figure 12:
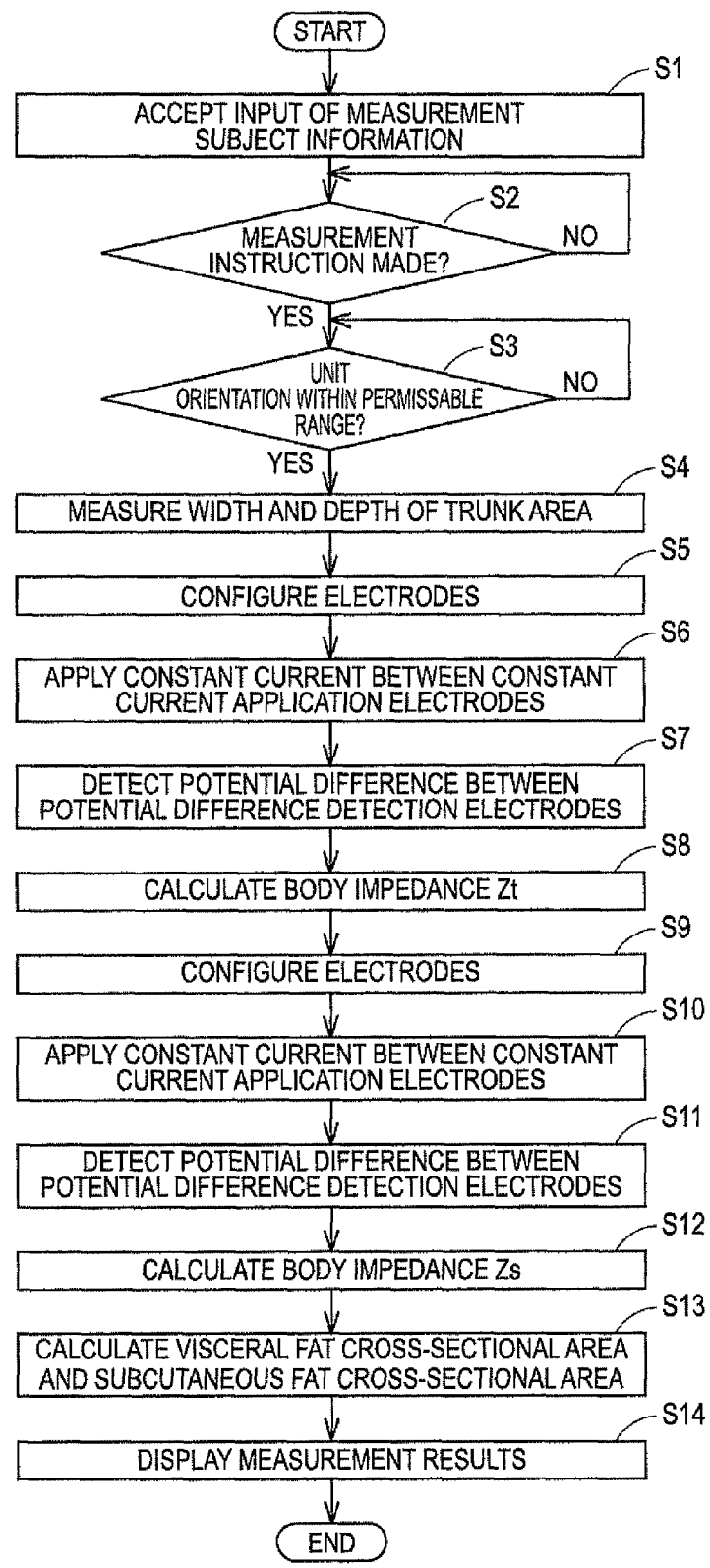
FIG. 12 is a flowchart illustrating a process performed by a control unit in the body fat measurement device according to the first embodiment of the present invention.

FIG. 12 is a flowchart illustrating a process performed by the control unit in the body fat measurement device according to the present embodiment. Next, a sequence of processes executed by the control unit of the body fat measurement device according to the present embodiment will be described with reference to FIG. 12. Note that the processes indicated in the flowchart in FIG. 12 are stored in the memory unit 29 in advance as a program, and a visceral fat cross-sectional area measurement process and a subcutaneous fat cross-sectional area measurement process are realized by the control unit 10 when the control unit 10 including the computation processing unit 11 reads out and executes that program.

As shown in FIG. 12, the control unit 10 first accepts an input of the measurement subject information (step S1). The accepted measurement subject information is temporarily saved in, for example, the memory unit 29.

Next, the control unit 10 determines whether or not there has been an instruction to start the measurement (step S2). The control unit 10 stands by until there has been an instruction to start the measurement (NO in step S2), and advances to the next process in the case where an instruction to start the measurement has been detected (YES in step S2). Note that the instruction to start the measurement is made by the measurement subject depressing the measure button 27a.

Next, the control unit 10 determines whether or not the orientation of the fitting unit 100A is within the permissible range (in other words, whether or not the fitting unit 100A is in a horizontal orientation) (step S3). Specifically, in the case where it has been determined that the fitting unit 100A is not within the stated permissible range based on a signal inputted from the unit orientation detection unit 30 (NO in step S3), the control unit 10 stands by until the fitting unit 100A is within the permissible range. At this time, the control unit 10 may carry out control prompting the measurement subject to adjust the orientation of the fitting unit 100A by displaying a guide in the display unit 26, warning the measurement subject that the orientation of the fitting unit 100A is not in a horizontal orientation by emitting a warning sound, or the like. On the other hand, in the case where it has been determined that the fitting unit 100A is within the permissible range based on a signal inputted from the unit orientation detection unit 30 (YES in step S3), the control unit 10 moves to the next process.

Next, the control unit 10 measures the width and depth of the trunk area (step S4). Specifically, the control unit 10 obtains the width 2a and the depth 2b of the trunk area of the measurement subject using the body shape information measurement unit 13, based on signals inputted from the trunk area width detection unit 24A and the trunk area depth detection unit 24B. The obtained width 2a and depth 2b of the trunk area of the measurement subject are temporarily saved in the memory unit 29.

Next, the control unit 10 configures the electrodes (step S5). Specifically, the control unit 10 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1A.

Next, the control unit 10 applies a constant current between the constant current application electrodes (step S6). Specifically, the control unit 10 outputs an instruction to the constant current generation unit 21 for generating the constant current, and based on this, the constant current generation unit 21 applies the constant current $I_A$ generated between the constant current application electrodes as shown in FIG. 1A.

Next, the control unit 10 detects a potential difference between the potential difference detection electrodes (step S7). Specifically, the control unit 10 outputs an instruction to the potential difference detection unit 23 for detecting a potential difference, and based on this, the potential difference detection unit 23 detects the potential differences $V_{A1}$, $V_{A2}$, $V_{A3}$, and $V_{A4}$ between the potential difference detection electrodes shown in FIG. 1A, and outputs the detected potential differences to the body impedance measurement unit 12.

Next, the control unit 10 calculates the body impedance Zt (step S8). Specifically, the control unit 10 calculates the body impedance Zt using the body impedance measurement unit 12, based on a signal inputted from the potential difference detection unit 23. The calculated body impedance Zt is temporarily saved in the memory unit 29.

Next, the control unit 10 reconfigures the electrodes (step S9). Specifically, the control unit 10 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1B.

Next, the control unit 10 applies a constant current between the constant current application electrodes (step S10). Specifically, the control unit 10 outputs an instruction to the constant current generation unit 21 for generating the constant current, and based on this, the constant current generation unit 21 applies the constant currents $I_{B1}$ and $I_{B2}$ generated between the constant current application electrodes as shown in FIG. 1B.

Next, the control unit 10 detects a potential difference between the potential difference detection electrodes (step S11). Specifically, the control unit 10 outputs an instruction to the potential difference detection unit 23 for detecting a potential difference, and based on this, the potential difference detection unit 23 detects the potential differences $V_{B1}$ and $V_{B2}$ between the potential difference detection electrodes shown in FIG. 1B, and outputs the detected potential differences to the body impedance measurement unit 12.

Next, the control unit 10 calculates the body impedance Zs (step S12). Specifically, the control unit 10 calculates the body impedance Zs using the body impedance measurement unit 12, based on a signal inputted from the potential difference detection unit 23. The calculated body impedance Zs is temporarily saved in the memory unit 29.

Next, the control unit 10 calculates the visceral fat cross-sectional area and the subcutaneous fat cross-sectional area (step S13). Specifically, the control unit 10 calculates the visceral fat cross-sectional area Sx as the visceral fat mass using the visceral fat mass calculation unit 14a and calculates the subcutaneous fat cross-sectional area Sb as the subcutaneous fat mass using the subcutaneous fat mass calculation unit 14b, based on the width 2a and depth 2b of the trunk area detected in step S4, the body impedance Zt calculated in step S8, and the body impedance Zs calculated in step S12 Note that the calculated visceral fat cross-sectional area Sx and subcutaneous fat cross-sectional area Sb are temporarily saved in the memory unit 29.

Then, the control unit 10 displays the measurement results (step S14). Specifically, the control unit 10 outputs, to the display unit 26, an instruction to display the visceral fat cross-sectional area Sx and subcutaneous fat cross-sectional area Sb calculated in step S13, and based on this, the display unit 26 displays those measurement results.

Through this, the body fat measurement device 1A completes the visceral fat cross-sectional area measurement process and the subcutaneous fat cross-sectional area measurement process. Note that a typical value for the body impedance Zt is approximately 5Ω, whereas a typical value for the body impedance Zs is approximately 80Ω.

Actions and Effects

With the body fat measurement device 1A according to the present embodiment as described thus far, the trunk area width detection unit 24A for detecting the trunk area width and the trunk area depth detection unit 24B for detecting the trunk area depth are provided in the fitting unit 100A for bringing the back area electrodes BU1-BU4 and BL1-BL4 into contact with the back area of the measurement subject in a pressurized state. In other words, the back area electrodes BU1-BU4 and BL1-BL4 and the trunk area width detection unit 24A and trunk area depth detection unit 24B are provided so as to be integrated with the fitting unit 100A that is configured as a single unit.

Therefore, with the body fat measurement device 1A according to the present embodiment, actual measurements can be taken of the trunk area width and trunk area depth with a high degree of accuracy in a state in which the fitting unit 100A is gripped and the back area electrodes BU1-BU4 and BL1-BL4 are pressed against the back area surface. Accordingly, the operations required of the measurement subject when measuring the body fat mass can be simplified, and the body fat mass can be measured accurately and easily through a simple operation, and furthermore, the measurement subject can carry out the measurement him/herself without help from an assistant or the like.

Furthermore, with the body fat measurement device according to the present embodiment as described thus far, the hand electrodes HR and HL serving as the upper limb electrodes are provided in an exposed state in the stated fitting unit 100A, in addition to the stated back area electrodes BU1-BU4 and BL1-BL4, trunk area width detection unit 24A, and trunk area depth detection unit 24B. In other words, the back area electrodes BU1-BU4 and BL1-BL4, the trunk area width detection unit 24A and trunk area depth detection unit 24B, and the hand electrodes HR and HL are provided so as to be integrated with the fitting unit 100A that is configured as a single unit.

Accordingly, by gripping the fitting unit 100A with the right hand and the left hand, the measurement subject can place the hand electrodes HR and HL in contact with the palm of his/her right hand and the palm of his/her left hand, respectively, and can place the back area electrodes BU1-BU4 and BL1-BL4 provided in the fitting unit 100A in contact with his/her back area surface by pressing the fitting unit 100A to the back area surface while gripping the fitting unit 100A with his/her right hand and left hand; furthermore, actual measurements of the trunk area width and the trunk area depth can be taken in this state with a high degree of accuracy.

Here, in the case where a configuration that places the electrodes in contact with the back area surface of the measurement subject is employed without employing the configuration of the body fat measurement device 1A according to the present embodiment as described above, it is difficult to maintain stable contact between the back area electrodes and the measurement subject's back area surface. Therefore, it is normally necessary for the measurement subject to lie face up or face down in order to stabilize the contact. In this case, it is extremely difficult for the measurement subject to carry out the measurement by him/herself without help from an assistant or the like, and as a result, the body fat measurement device cannot be used effectively in a household or the like.

However, as described above, with the body fat measurement device 1A according to the present embodiment, the back area electrodes BU1-BU4 and BL1-BL4, the trunk area width detection unit 24A and trunk area depth detection unit 24B, and the hand electrodes HR and HL are provided so as to be integrated with the fitting unit 100A that is configured as a single unit, and thus the back area electrodes BU1-BU4 and BL1-BL4 can, with a simple operation, be brought into contact, in a stable manner, with the back area surface of the measurement subject who is standing up; in addition, the state of stable contact between the back area electrodes BU1-BU4 and BL1-BL4 and the measurement subject's back area surface can be maintained during the measurement operations, and furthermore, actual measurements can be taken of the trunk area width and the trunk area depth in such a state with a high degree of accuracy. Accordingly, with the body fat measurement device 1A according to the present embodiment, the operations required of the measurement subject when measuring the body fat mass can be simplified, and the body fat mass can be measured accurately and easily through a simple operation, and furthermore, the measurement subject can carry out the measurement him/herself without help from an assistant or the like.

Furthermore, with the body fat measurement device 1A according to the present embodiment, body fat mass such as the visceral fat mass, the subcutaneous fat mass, and so on can be measured while the back area electrodes BU1-BU4 and BL1-BL4 are placed in contact with the back area surface of the measurement subject, and thus instead of a current being locally applied to the abdominal area, where the subcutaneous fat is relatively thin, a current can be locally applied to the back area, where the subcutaneous fat is relatively thick; thus the body fat mass can be measured with a higher degree of accuracy.

Accordingly, the body fat measurement device 1A according to the present embodiment makes it possible to realize a body fat measurement device capable of measuring body fat mass, such as visceral fat mass and subcutaneous fat mass, easily and accurately within a household or the like. Therefore, using the body fat measurement device 1A makes it possible to obtain such indicators for health management on a daily basis.

Figure 13:
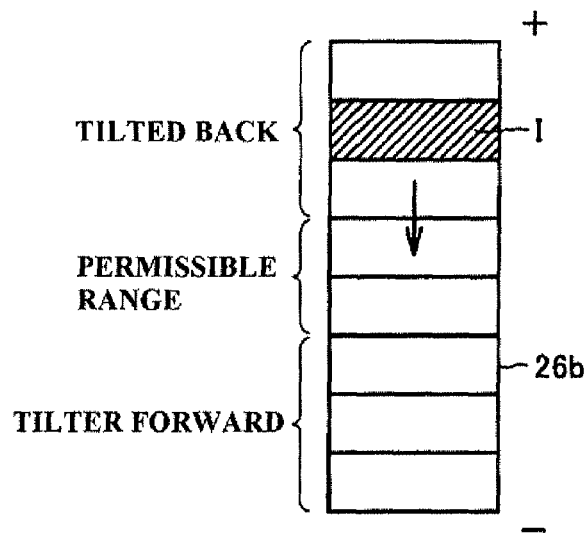
FIG. 13 is a diagram illustrating another example of a display in the second display unit that displays an orientation of the fitting unit of the body fat measurement device according to the first embodiment of the present invention.

FIG. 13 is a diagram illustrating another example of a display in the second display unit that displays the orientation of the fitting unit of the body fat measurement device according to the present embodiment.

Although the example of the display shown in the aforementioned FIG. 11 illustrates a configuration in which the orientation can be detected in both the depth direction and the horizontal direction of the fitting unit 100A, employing the measurement position described above tends to make it easy to maintain the fitting unit 100A in a horizontal orientation in the horizontal direction. However, employing the measurement position described above also tends to make it difficult to maintain the fitting unit 100A in a horizontal orientation in the depth direction.

Accordingly, in order to further simplify the device configuration, it is possible to configure the device so as to detect only the orientation of the fitting unit 100A in the depth direction, and to configure the second display unit 26b that displays the orientation of the fitting unit 100A in the manner shown in FIG. 13.

In other words, in the example of the display shown in FIG. 13, regions indicating the degree of the tilt of the fitting unit 100A in the depth direction thereof are arranged along the depth direction of the second display unit 26b, and the indicator I is displayed by lighting a region that corresponds to the result of the detection performed by the unit orientation detection unit 30.

The display state shown in FIG. 13 indicates a state in which the forward area of the fitting unit 100A (that is, the area of connection located toward the front frame portion 114) is higher than the rear area, and thus the measurement subject adjusts the orientation of the fitting unit 100A so that the indicator I falls within a region indicated as the aforementioned permissible range.

Second Embodiment

Figure 14:
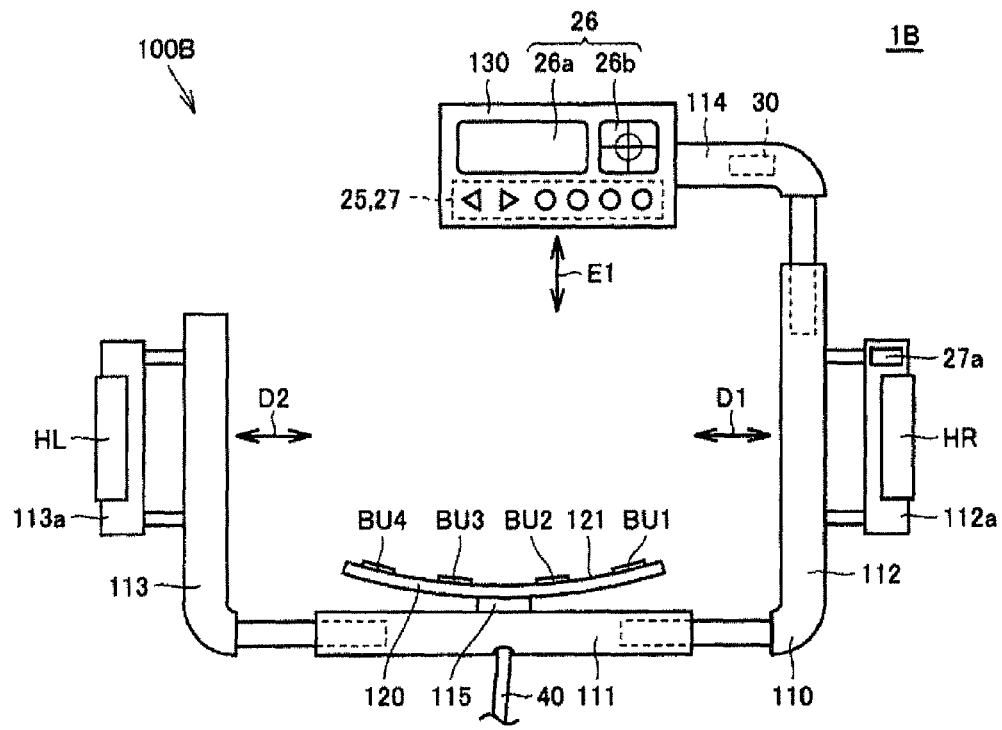
FIG. 14 is a top view of a fitting unit of a body fat measurement device according to a second embodiment of the present invention.
Figure 15:
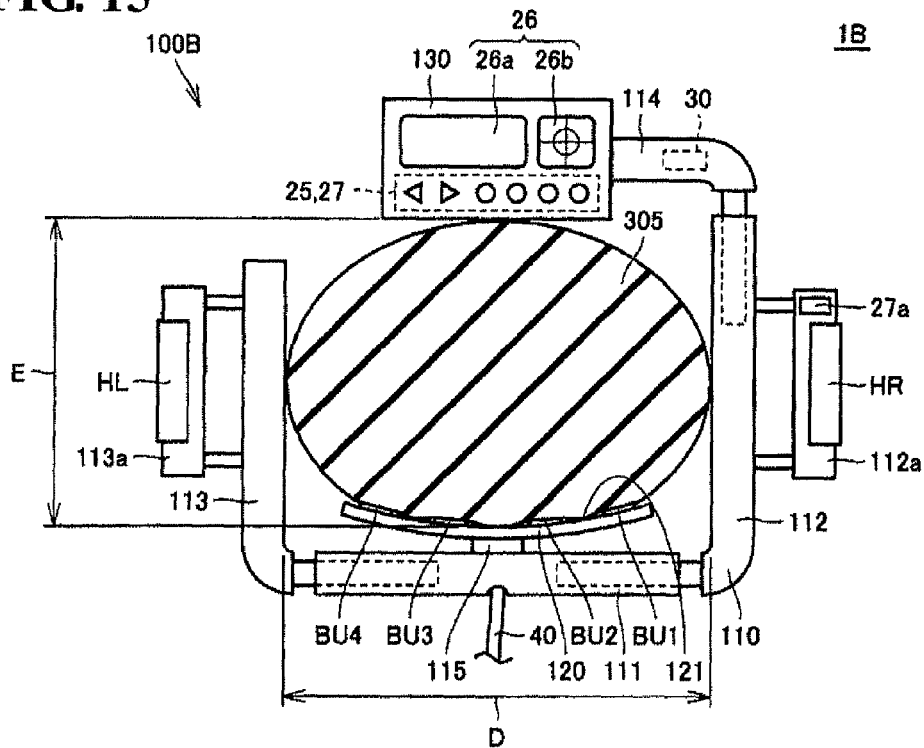
FIG. 15 is a diagram illustrating a fitted state of the fitting unit of the body fat measurement device according to the second embodiment of the present invention.

FIG. 14 is a top view of a fitting unit of a body fat measurement device according to a second embodiment of the present invention, and FIG. 15 is a diagram illustrating a fitted state of the fitting unit of the body fat measurement device according to the present embodiment. Next, details of the structure of the fitting unit of the body fat measurement device according to the present embodiment, and a fitted state of the fitting unit, will be described with reference to FIGS. 14 and 15. Note that the fundamentals of the measurement performed by the body fat measurement device and the computation processes executed by the control unit according to the present embodiment are the same as those of the body fat measurement device according to the aforementioned first embodiment of the present invention.

As shown in FIG. 14, a body fat measurement device 1B according to the present embodiment includes, like the body fat measurement device 1A according to the aforementioned first embodiment of the present invention, a fitting unit 100B having a frame shape capable of being disposed so as to surround the trunk area of the measurement subject in a fitted state, and the platform unit 200 (not shown; see FIG. 3 and so on) shaped as a platform onto which the measurement subject can step.

The fitting unit 100B of the body fat measurement device 1B according to the present embodiment is configured so that the rear frame portion 111, the right-side frame portion 112, the left-side frame portion 113, and the front frame portion 114 of the frame member 110 are divided into individual units, and the rear frame portion 111, the right-side frame portion 112, the left-side frame portion 113, and the front frame portion 114 are each linked to their respective adjacent frame portions so as to be capable of moving relative thereto.

To be more specific, the right-side frame portion 112 is configured so as to be capable of moving relative to the rear frame portion 111 in the direction of an arrow D1 shown in FIG. 14, the left-side frame portion 113 is configured so as to be capable of moving relative to the rear frame portion 111 in the direction of an arrow D2 shown in FIG. 14, and the front frame portion 114 is configured so as to be capable of moving relative to the right-side frame portion 112 in the direction of an arrow E1 shown in FIG. 14.

Furthermore, with the body fat measurement device 1B according to the present embodiment, handle portions 112a and 113a are provided projecting outward from the right-side frame portion 112 and the left-side frame portion 113, respectively, and the hand electrodes HR and HL are provided on the handle portions 112a and 113a, respectively, in an exposed state.

Here, the body fat measurement device 1B according to the present embodiment does not include the non-contact optical sensor provided in the body fat measurement device 1A according to the aforementioned first embodiment of the present invention; instead, a movement amount detection sensor that serves as the trunk area width detection unit 24A and detects the relative amount of movement between the stated right-side frame portion 112 and left-side frame portion 113 and the rear frame portion 111, and a movement amount detection sensor that serves as the trunk area depth detection unit 24B and detects the relative amount of movement between the stated front frame portion 114 and the right-side frame portion 112, are provided in the fitting unit 100A. A variety of elements, including various types of encoders such as rotary encoders, optical sensors, magnetic sensors, and so on, can be used as the movement amount detection sensors.

As shown in FIG. 15, when the fitting unit 100B is in the fitted state, the trunk area 305 of the measurement subject is surrounded by the frame member 110, and the abdominal area, back area, and both side areas of the trunk area 305 are in contact with the fitting unit 100B.

In order to achieve this state, the measurement subject grips the handle portions 112a and 113a with his/her right hand and left hand, respectively, so that the palms of his/her right hand and left hand make contact with the hand electrodes HR and HL, respectively; while maintaining this grip, the measurement subject adjusts the position of the fitting unit 100B so that the front surface 121 of the electrode support member 120 provided in the fitting unit 100B makes contact with his/her back area surface.

At this time, the measurement subject moves the right-side frame portion 112 and the left-side frame portion 113 so that an inner side area of the right-side frame portion 112 and an inner side area of the left-side frame portion 113 make contact with both sides of the trunk area 305 (that is, both flanks), respectively; the measurement subject then releases one hand, moves the front frame portion 114 so that the rear surface of the display unit portion 130 makes contact with a front area of the trunk area (in other words, the abdominal area), and then returns the released hand back to its original position.

Furthermore, at this time, the measurement subject adjusts the orientation of the fitting unit 100B so that the fitting unit 100B is positioned horizontally, while viewing and referring to the second display unit 26b that displays the orientation of the fitting unit 100B in a visible state. As a result, the fitting unit 100B enters the fitted state shown in FIG. 15, and the measurement of body fat mass can be started.

Here, assuming that the positions of the right-side frame portion 112, the left-side frame portion 113, and the front frame portion 114 shown in FIG. 14 are the starting points, the amounts by which the right-side frame portion 112, the left-side frame portion 113, and the front frame portion 114 move from the starting points shown in FIG. 14 until those frame portions reach the positions shown in FIG. 15 are measured by the stated movement amount detection sensors, and thus, as shown in FIG. 15, the width 2a of the trunk area is calculated as a distance D, and the depth 2b of the trunk area is calculated as a distance E.

With the body fat measurement device 1B according to the present embodiment as described thus far, the same effects as those described in the aforementioned first embodiment of the present invention can be achieved.

Third Embodiment

Figure 16:
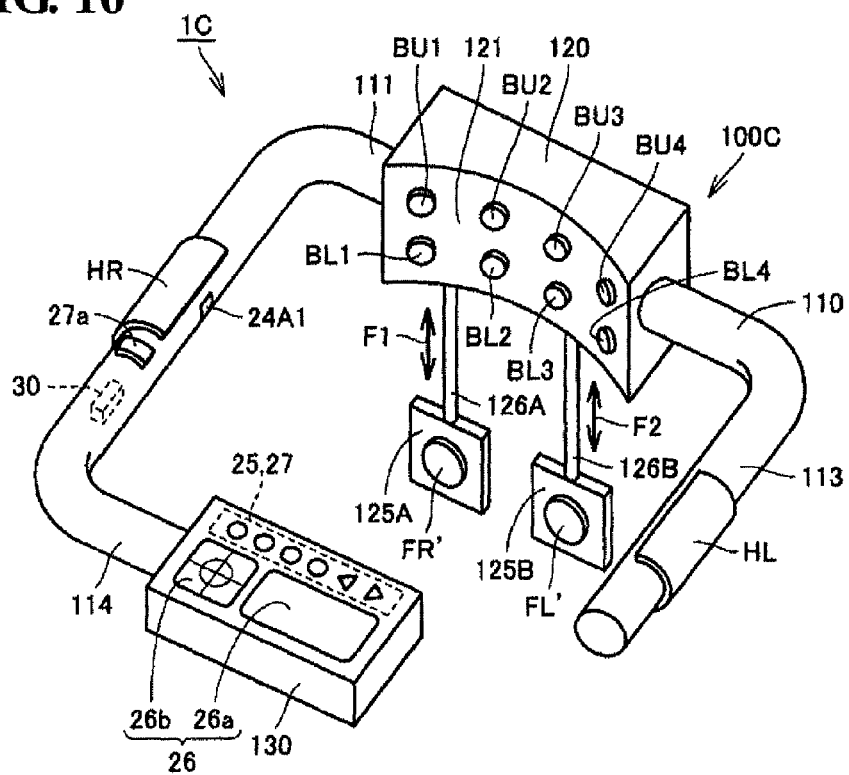
FIG. 16 is a perspective view illustrating a body fat measurement device according to a third embodiment of the present invention.

FIG. 16 is a perspective view illustrating a body fat measurement device according to a third embodiment of the present invention. Next, the structure of the body fat measurement device according to the present embodiment will be described in detail with reference to FIG. 16. Note that the fundamentals of the measurement performed by the body fat measurement device and the computation processes executed by the control unit according to the present embodiment are the same as those of the body fat measurement device according to the aforementioned first embodiment of the present invention.

As shown in FIG. 16, a body fat measurement device 1C according to the present embodiment includes, like the body fat measurement device 1A according to the aforementioned first embodiment of the present invention, a fitting unit 100C having a frame shape capable of being disposed so as to surround the trunk area of the measurement subject in a fitted state. However, unlike the body fat measurement device 1A according to the aforementioned first embodiment of the present invention, the body fat measurement device 1C according to the present embodiment does not include a platform-shaped platform unit onto which the measurement subject can step; instead, electrode pads 125A and 125B, serving as extending unit portions configured so as to be extendable from the fitting unit 100C, are provided.

The electrode pads 125A and 125B have approximate plate shapes, and foot/hip electrodes FL' and FR', serving as lower limb/hip electrodes for making contact with the surface of the respective lower limbs or hips, are provided in an exposed state on the main surfaces of the electrode pads 125A and 125B, respectively. The one ends of connection cables 126A and 126B are attached to upper areas of the electrode pads 125A and 125B, respectively, and the other ends of the connection cables 126A and 126B are anchored to reel members provided within the electrode support member 120. Note that in the fitting unit 100C according to the present embodiment, the electrode support member 120 is configured as a block-shaped member in order to make it possible to dispose the reel members within the electrode support member 120, and the electrode support member 120 is attached in approximately the center of the rear frame portion 111 of the frame member 110.

Through this, the electrode pads 125A and 125B can be extended downward from the fitting unit 100C by pulling the connection cables 126A and 126B, which serve as connection lines, in the direction of arrows F1 and F2 shown in FIG. 16. In other words, by adjusting the extension amount of the connection cables 126A and 126B, the electrode pads 125A and 125B can be attached at desired locations, such as the lower limbs, the hips, and so on of the measurement subject.

With the body fat measurement device 1C according to the present embodiment as described thus far, the same effects as those described in the aforementioned first embodiment of the present invention can be achieved. In addition, with the body fat measurement device 1C according to the present embodiment, the measurement can be carried out in a seated position as well as a standing position, which makes it even easier to measure body fat mass. Furthermore, with the body fat measurement device 1C according to the present embodiment, there is no platform unit, and thus the device configuration can be simplified and the size of the device can be reduced.

Note that pads that attach to the measurement subject's body through suction, through and adhesive, or that are attached by being wrapped around the measurement subject's body using some sort of wrapping member can be used as the electrode pads 125A and 125B; furthermore, pads that are not particularly attached but are anchored by being sandwiched between the measurement subject's body and a seating surface, a floor surface, or the like can be used as the electrode pads 125A and 125B.

Fourth Embodiment

Figure 17A:
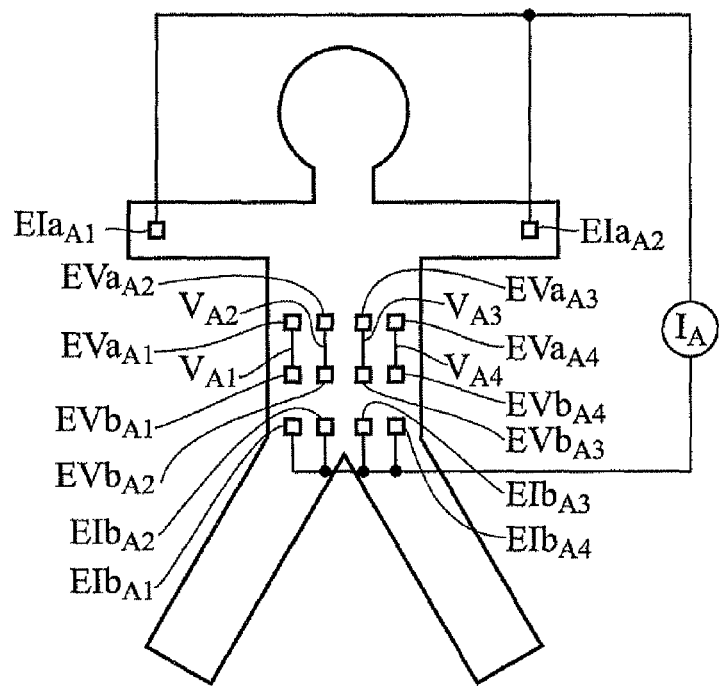
FIGS. 17A and 17B are diagrams illustrating the fundamentals of measurement performed by a body fat measurement device according to a fourth embodiment of the present invention.
Figure 17B:
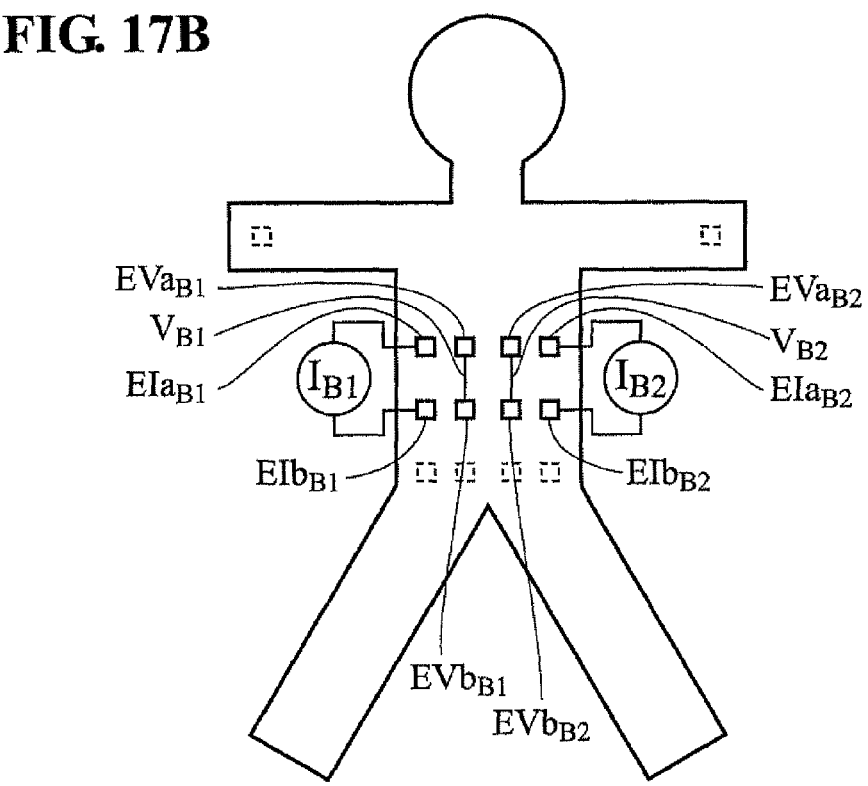

FIGS. 17A and 17B are diagrams illustrating the fundamentals of measurement performed by a body fat measurement device according to a fourth embodiment of the present invention. Here, FIG. 17A is a diagram illustrating the placement of electrodes when obtaining a body impedance for the entire trunk area, whereas FIG. 17B is a diagram illustrating the placement of electrodes when obtaining a body impedance for a surface layer area on the back area side of the trunk area. First, the fundamentals of measurement performed by the body fat measurement device according to the present embodiment will be described with reference to FIGS. 17A and 17B. Note that FIGS. 17A and 17B both illustrate the measurement subject from the back side thereof.

The fundamentals of the measurement performed by the body fat measurement device according to the present embodiment are also basically the same as the fundamentals of the measurement described in the aforementioned first embodiment of the present invention. However, the positions in which the electrodes used when obtaining the body impedance of the entire trunk area are placed are slightly different from those in the aforementioned first embodiment of the present invention.

Specifically, as shown in FIG. 17A, electrodes $EIa_{A1}$ and $EIa_{A2}$ are attached to the surface of the left hand of the measurement subject and the surface of the right hand of the measurement subject, respectively, in order to obtain the body impedance for the entire trunk area. Meanwhile, four pairs of electrodes are attached to the back area surface of the measurement subject, with each pair disposed so as to follow the body axis direction, and with the four pairs arranged in the widthwise direction of the trunk area; furthermore, four electrodes are attached to an area of the back area surface that is closer to the hip area than the contact locations where the stated four pairs of electrodes are placed, with these four electrodes being arranged along the widthwise direction of the trunk area. In other words, as shown in FIG. 17A, a total of twelve electrodes, or electrodes $EVa_{A1}$, $EVb_{A1}$, $EVa_{A2}$, $EVb_{A2}$, $EVa_{A3}$, $EVb_{A3}$, $EVa_{A4}$, $EVb_{A4}$, $EIb_{A1}$, $EIb_{A2}$, $EIb_{A3}$, and $EIb_{A4}$, are attached to the back area surface of the measurement subject.

In this state, a constant current $I_A$ that passes through the trunk area is applied to the measurement subject using the electrodes $EIa_{A1}$, $EIa_{A2}$, $EIb_{A1}$, $EIb_{A2}$, $EIb_{A3}$, and $EIb_{A4}$ attached to both hands and the back area near the hip area, respectively. While the constant current $I_A$ is applied, a potential difference $V_{A1}$ is detected using the pair of electrodes $EVa_{A1}$ and $EVb_{A1}$ attached to the back area surface, a potential difference $V_{A2}$ is detected using the pair of electrodes $EVa_{A2}$ and $EVb_{A2}$ attached to the back area surface, a potential difference $V_{A3}$ is detected using the pair of electrodes $EVa_{A3}$ and $EVb_{A3}$ attached to the back area surface, and a potential difference $V_{A4}$ is detected using the pair of electrodes $EVa_{A4}$ and $EVb_{A4}$ attached to the back area surface.

With a body fat measurement device 1D according to the present embodiment, a body impedance Zt of the entire trunk area is calculated from the potential differences $V_{A1}$, $V_{A2}$, $V_{A3}$, and $V_{A4}$ detected in this manner. Note that the placement of electrodes, the constant current application, and the potential difference detection for obtaining the body impedance Zs of the surface layer area on the back area of the trunk area are, as shown in FIG. 17B, all the same as those in the aforementioned first embodiment of the present invention.

Figure 18:
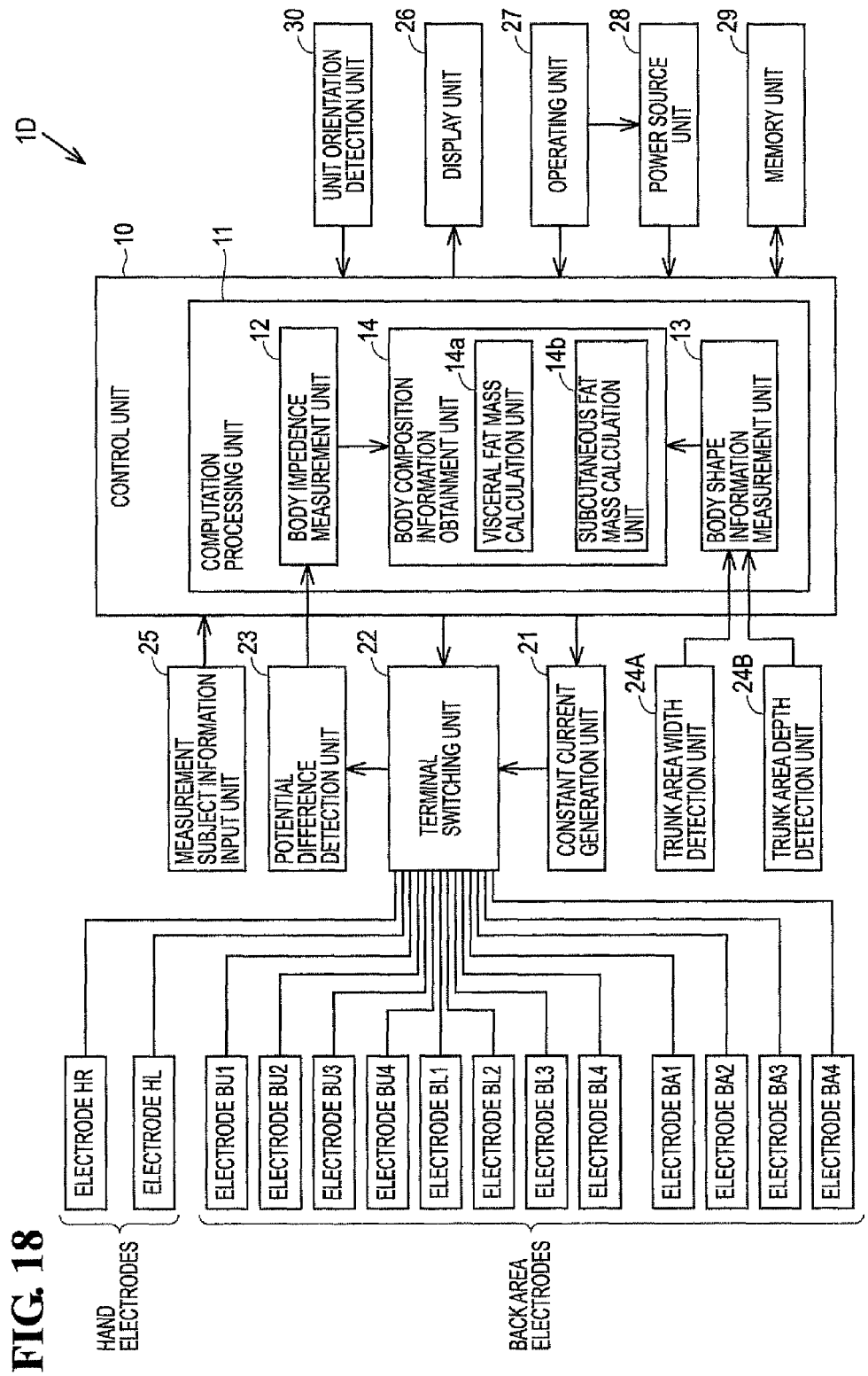
FIG. 18 is a diagram illustrating the functional block configuration of the body fat measurement device according to the fourth embodiment of the present invention.

FIG. 18 is a diagram illustrating the functional block configuration of the body fat measurement device according to the present embodiment. Next, the functional block configuration of the body fat measurement device according to the present embodiment will be described with reference to FIG. 18.

As shown in FIG. 18, the body fat measurement device 1D according to the present embodiment has a similar configuration as the body fat measurement device 1A according to the aforementioned first embodiment of the present invention, but differs slightly in terms of the configuration of the multiple electrodes connected to the terminal switching unit 22. In other words, the body fat measurement device 1D according to the present embodiment includes electrodes HR, HL, BU1-BU4, BL1-BL4, and BA1-BA4 as the multiple electrodes.

The aforementioned multiple electrodes include: hand electrodes HR and HL serving as upper limb electrodes placed in contact with surfaces of the upper limbs of the measurement subject; and back area electrodes BU1-BU4, BL1-BL4, and BA1-BA4 placed in contact with the back area surface of the measurement subject. Of these, the hand electrodes HR and HL are placed in contact with the palms of the measurement subject's hands. Meanwhile, as shown in FIGS. 17A and 17B, the back area electrodes BU1-BU4, BL1-BL4, and BA1-BA4 are arranged in rows and placed in contact with the back area surface of the measurement subject. Note that the hand electrodes HR and HL and the back area electrodes BU1-BU4, BL1-BL4, and BA1-BA4 are all electrically connected to the terminal switching unit 22 described above.

Figure 19:
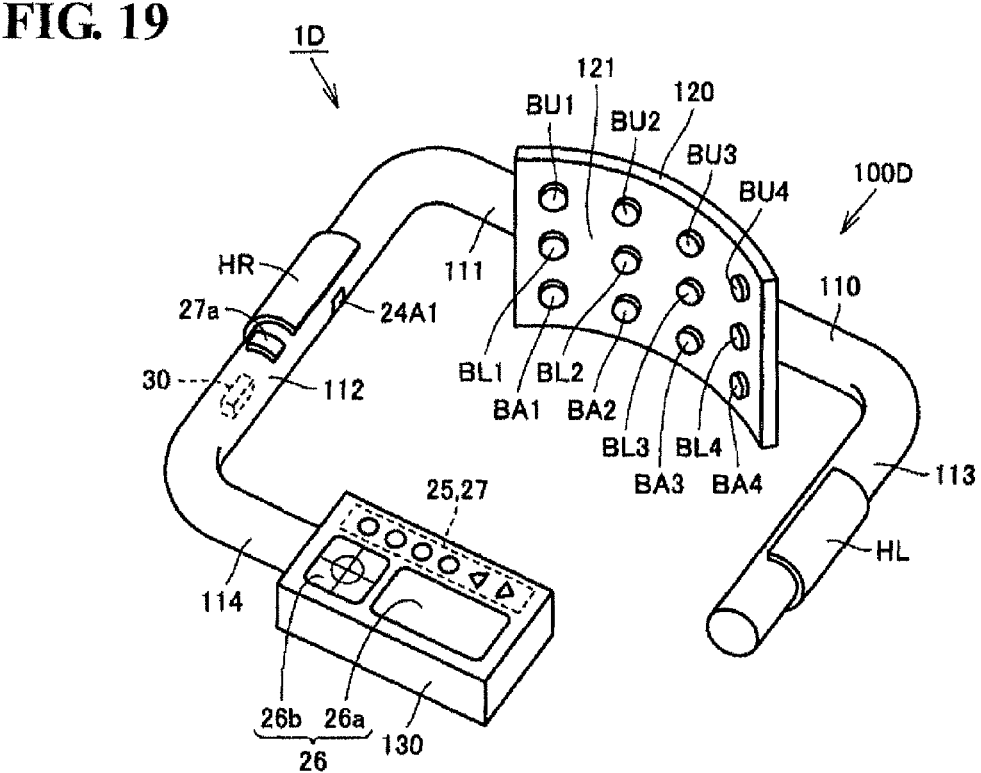
FIG. 19 is a perspective view illustrating the body fat measurement device according to the fourth embodiment of the present invention.

FIG. 19 is a perspective view illustrating the body fat measurement device according to the present embodiment. Next, the structure of the body fat measurement device according to the present embodiment will be described in detail with reference to FIG. 19.

As shown in FIG. 19, the body fat measurement device 1D according to the present embodiment includes, like the body fat measurement device 1A according to the aforementioned first embodiment of the present invention, a fitting unit 100D having a frame shape capable of being disposed so as to surround the trunk area of the measurement subject in a fitted state. However, unlike the body fat measurement device 1A according to the aforementioned first embodiment of the present invention, the body fat measurement device 1D according to the present embodiment does not include a platform-shaped platform unit onto which the measurement subject can step. Instead, with the body fat measurement device 1D according to the present embodiment, the back area electrodes BA1-BA4 are further provided on the electrode support member 120 attached to the frame member 110.

To be more specific, the electrode support member 120, which is configured of a curved plate, extends further downward than in the aforementioned first embodiment of the present invention, and the back area electrodes BA1-BA4 are provided on the front surface 121 of the area of the electrode support member 120 that has been extended. Here, the back area electrodes BA1-BA4 are provided so that all the electrodes are exposed on the front surface 121 of the electrode support member 120, and preferably, the back area electrodes BA1-BA4 protrude slightly from the front surface 121 of the electrode support member 120. Through this, the back area electrodes BA1-BA4 are, like the back area electrodes BU1-BU4 and BL1-BL4, placed in contact with the back area surface of the measurement subject during the fitted state.

With the body fat measurement device 1D according to the present embodiment as described thus far, the same effects as those described in the aforementioned first embodiment of the present invention can be achieved. In addition, with the body fat measurement device 1D according to the present embodiment, the measurement can be carried out in a seated position as well as a standing position, which makes it even easier to measure body fat mass. Furthermore, with the body fat measurement device 1D according to the present embodiment, there is no platform unit, and thus the device configuration can be simplified and the size of the device can be reduced.

Fifth Embodiment

Figure 20:
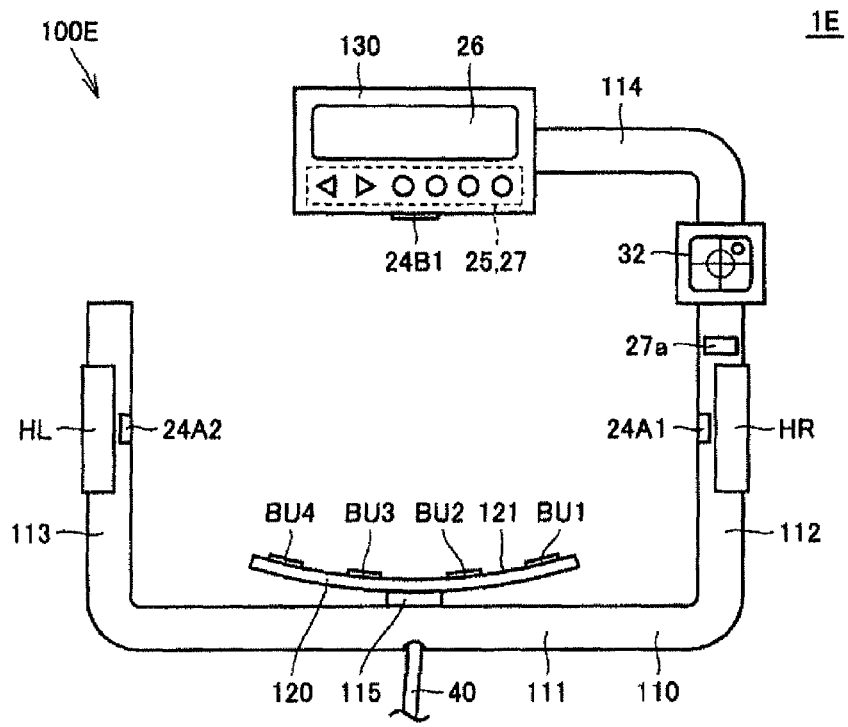
FIG. 20 is a top view of a fitting unit of a body fat measurement device according to a fifth embodiment of the present invention.
Figure 21:
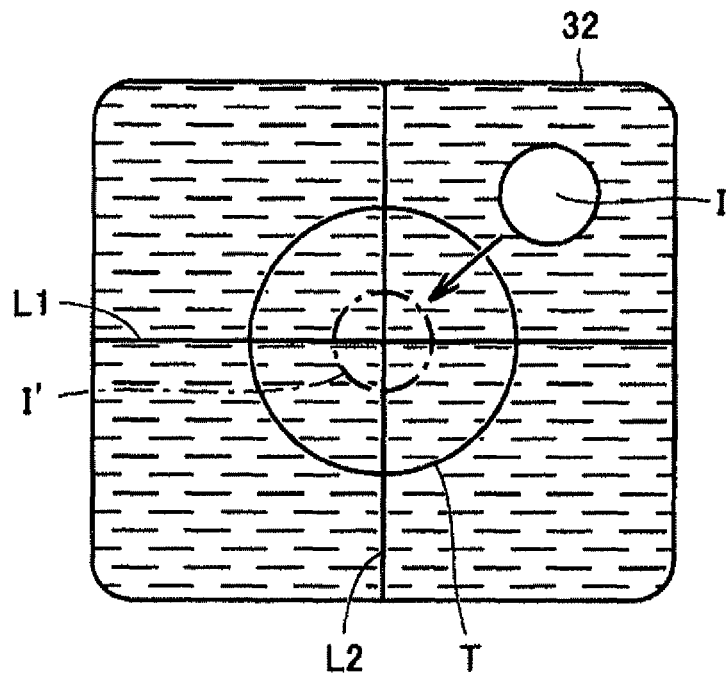
FIG. 21 is a diagram illustrating a level provided in the body fat measurement device according to the fifth embodiment of the present invention.

FIG. 20 is a top view illustrating a fitting unit of a body fat measurement device according to a fifth embodiment of the present invention. Meanwhile, FIG. 21 is a diagram illustrating a level provided in the body fat measurement device according to the present embodiment. Next, the structure of the body fat measurement device according to the present embodiment will be described in detail with reference to FIGS. 20 and 21. Note that the fundamentals of the measurement performed by the body fat measurement device and the computation processes executed by the control unit according to the present embodiment are the same as those of the body fat measurement device according to the aforementioned first embodiment of the present invention.

As shown in FIG. 20, a body fat measurement device 1E according to the present embodiment includes, like the body fat measurement device 1A according to the aforementioned first embodiment of the present invention, a fitting unit 100E having a frame shape capable of being disposed so as to surround the trunk area of the measurement subject in a fitted state, and a platform unit 200 (not shown; see FIG. 3 and the like) shaped as a platform onto which the measurement subject can step.

However, in the body fat measurement device 1E according to the present embodiment, the accelerometer serving as the unit orientation detection unit and the second display unit that displays the orientation of the fitting unit included in the body fat measurement device 1A according to the aforementioned first embodiment of the present invention are not provided in the fitting unit 100E; instead, a level 32 is provided in the fitting unit 100E.

Here, the level 32 is an element that indicates the orientation of the fitting unit 100E, and is configured, for example, with a fluid containing a bubble of a predetermined size sealed within a receptacle, where the top surface of the receptacle is transparent so that the inside of the receptacle is visible. Specifically, the level 32 is provided in the vicinity of the front end of the right-side frame portion 112 of the frame member 110 in the fitting unit 100E.

As shown in FIG. 21, a guide line L1 that represents the horizontal direction of the fitting unit 100E and a guide line L2 that represents the depth direction of the fitting unit 100E are indicated on the top surface of the level 32, and furthermore, a region T expressing a permissible range of the orientation of the fitting unit 100E is indicated, in an ancillary manner, as a circle in the center of which the guide line L1 and the guide line L2 intersect. An indicator I, which corresponds to the bubble, is positioned toward the top surface of the level 32.

Here, the state shown in FIG. 21 indicates that a right-front area of the fitting unit 100E (that is, the area of connection between the right-side frame portion 112 and the front frame portion 114) is lower than the other areas, and thus the measurement subject adjusts the orientation of the fitting unit 100E so that the indicator I, which corresponds to the bubble, falls within the aforementioned region T that expresses the permissible range (that is, so that the indicator I, which corresponds to the bubble, moves to the position indicated by I', shown as a broken circle in FIG. 21).

With the body fat measurement device 1E according to the present embodiment as described thus far, the same effects as those described in the aforementioned first embodiment of the present invention can be achieved. In addition, the body fat measurement device 1E according to the present embodiment uses the level 32, which is comparatively cheap and can be incorporated into the device with ease, as the component for ensuring that the orientation of the fitting unit 100E is kept in the horizontal orientation; thus the body fat measurement device can be manufactured at a lower cost and more easily than the body fat measurement device according to the aforementioned first embodiment of the present invention.

Figure 22:
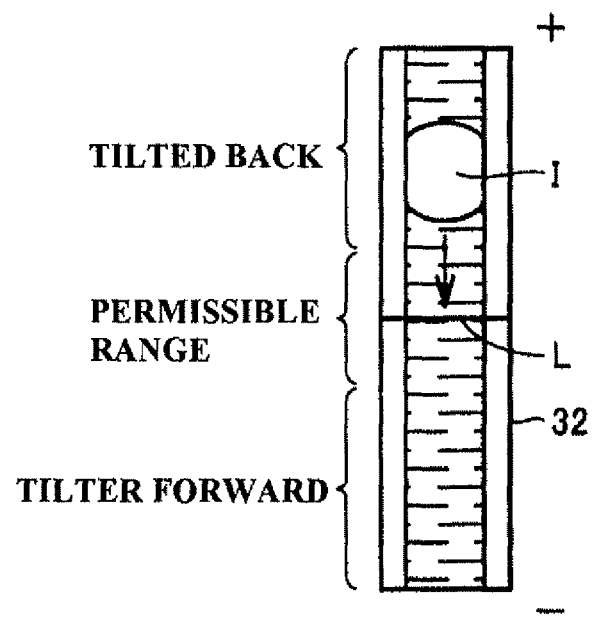
FIG. 22 is a diagram illustrating another example of a level provided in the body fat measurement device according to the fifth embodiment of the present invention.

FIG. 22 is a diagram illustrating another example of a level provided in the body fat measurement device according to the present embodiment.

Although the levels illustrated in the aforementioned FIGS. 20 and 21 are configured so that the orientation of the fitting unit 100E in both the depth direction and the horizontal direction thereof can be visually confirmed, employing the measurement position described above tends to make it easy to maintain the orientation of the fitting unit 100E in a horizontal orientation. However, employing the measurement position described above also tends to make it difficult to maintain the fitting unit 100E in a horizontal orientation in the depth direction.

Accordingly, in order to further simplify the device configuration, it is possible to configure the level 32 so that only the orientation of the fitting unit 100E in the depth direction thereof can be visually confirmed.

In other words, with the level 32 shown in FIG. 22, the receptacle in which the liquid is sealed is longer in the depth direction, and only a guide line L that indicates the horizontal direction of the fitting unit 100E is shown on the top surface of the level 32. An indicator I, which corresponds to the bubble, is positioned toward the top surface of the level 32.

Here, the state shown in FIG. 22 illustrates a state in which the front area of the fitting unit 100E (that is, the area of connection located toward the front frame portion 114) is higher than the rear area, and thus the measurement subject adjusts the orientation of the fitting unit 100E so that the indicator I, which corresponds to the bubble, matches with the guide line L that indicates the center of the permissible range.

Sixth Embodiment

Figure 23:
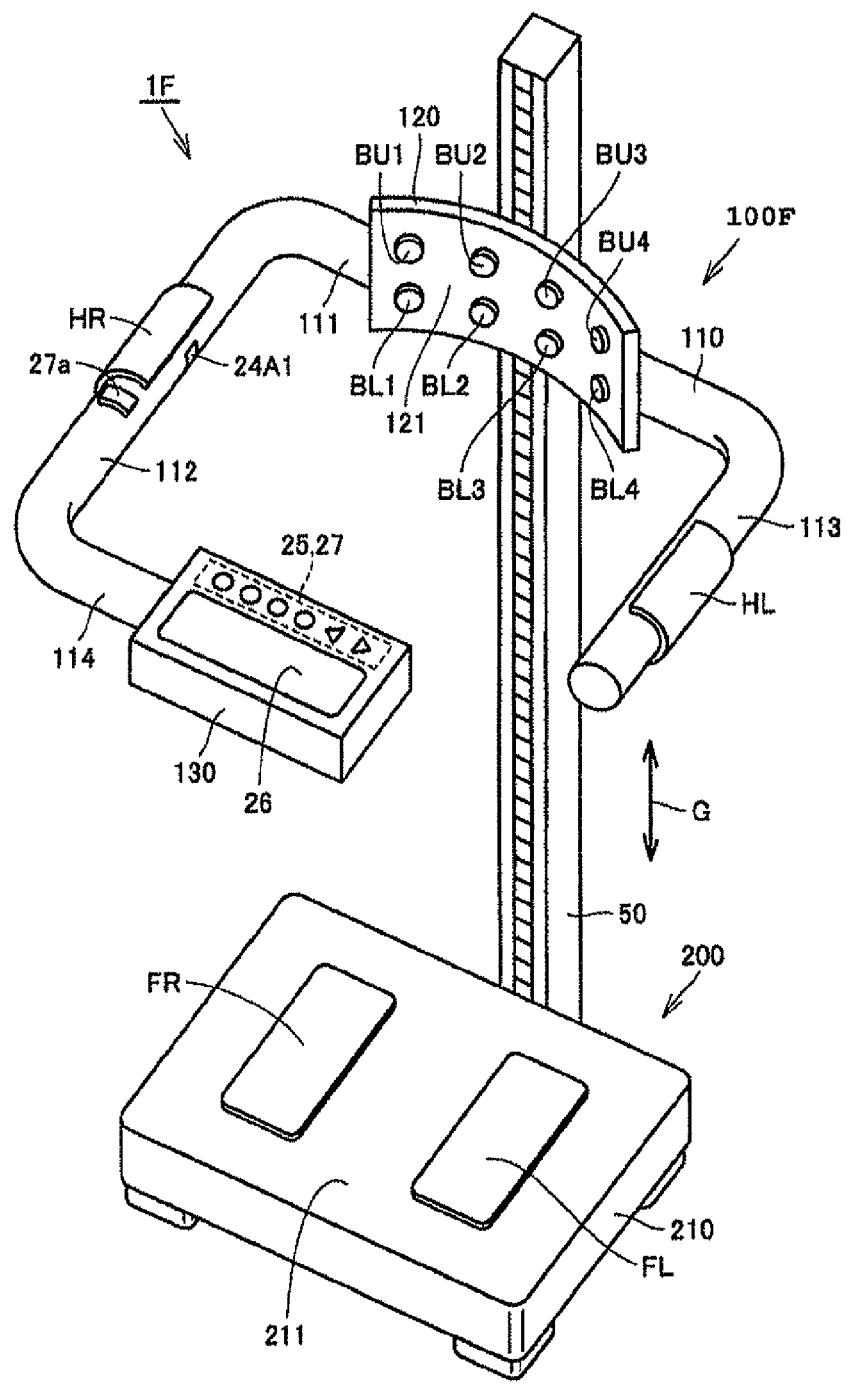
FIG. 23 is a perspective view illustrating a body fat measurement device according to a sixth embodiment of the present invention.

FIG. 23 is a perspective view illustrating a body fat measurement device according to a sixth embodiment of the present invention. Next, the structure of the body fat measurement device according to the present embodiment will be described in detail with reference to FIG. 23. Note that the fundamentals of the measurement performed by the body fat measurement device and the computation processes executed by the control unit according to the present embodiment are the same as those of the body fat measurement device according to the aforementioned first embodiment of the present invention.

As shown in FIG. 23, a body fat measurement device 1F according to the present embodiment includes, like the body fat measurement device 1A according to the aforementioned first embodiment of the present invention, a fitting unit 100F having a frame shape capable of being disposed so as to surround the trunk area of the measurement subject in a fitted state, and the platform unit 200 shaped as a platform onto which the measurement subject can step.

However, in the body fat measurement device 1F according to the present embodiment, the accelerometer serving as the unit orientation detection unit and the second display unit that displays the orientation of the fitting unit included in the body fat measurement device 1A according to the aforementioned first embodiment of the present invention are not provided in the fitting unit 100F; instead, the fitting unit 100F and the platform unit 200 are linked by a support column portion 50.

Specifically, as shown in FIG. 23, the support column portion 50 is erected on the rear area of the platform unit 200 so as to extend upward vertically, and the rear area of the fitting unit 100F is supported by the support column portion 50. Here, the fitting unit 100F is supported by the support column portion 50 in a mobile state so that the position of the fitting unit 100F in the vertical direction (the direction of the arrow G in FIG. 23) can be adjusted in a variable manner while maintaining the horizontal orientation thereof. Note that when fitting the fitting unit 100F, the measurement subject may adjust the height of the fitting unit 100F and place the fitting unit 100F in a position that surrounds the trunk area.

With the body fat measurement device 1F according to the present embodiment as described thus far, the same effects as those described in the aforementioned first embodiment of the present invention can be achieved. In addition, with the body fat measurement device 1F according to the present embodiment, providing the support column portion 50 makes it possible to employ a configuration in which the orientation of the fitting unity 100F is constantly maintained comparatively easily and accurately, and thus the body fat measurement can be carried out more accurately and easily than in the aforementioned first embodiment of the present invention.

In addition, with the body fat measurement device 1F according to the present embodiment, the fitting unit 100F may be attached to the support column portion 50 so as to be capable of pivoting. Specifically, the configuration may be such that a hinge or the like serving as a pivoting link portion is provided on at the area of the fitting unit 100F that is attached to the support column portion 50, and the front area of the fitting unit 100F can pivot upward and/or downward. By employing such a configuration, it is possible to fold the fitting unit 100F toward the support column portion 50 when not in use (in other words, to put the fitting unit 100F in a vertical orientation), which results in a device having superior storability. Furthermore, the platform unit 200 may be attached to the support column portion 50 so as to be capable of pivoting in the same manner as the fitting unit 100F, and the platform unit 200 may be flipped up toward the support column portion 50 when not in use, resulting in even further improved storability.

Although the first through sixth embodiments of the present invention described above describe examples in which the hand electrodes HR and HL are respectively provided in the right-side frame portion 112 and the left-side frame portion 113 of the frame member 110 in the fitting units 100A through 100F, it should be noted that the hand electrodes HR and HL may be provided in the front frame portion 114 of the frame member 110, and, depending on the situation, may not be provided in the fitting unit.

In addition, although the aforementioned first through sixth embodiments of the present invention have describe examples in which part of the frame member 110 in the fitting units 100A through 100F is not continuous, the configuration may be such that the shape is continuous.

In addition, although the aforementioned first through sixth embodiments of the present invention have described examples in which the frame member 110 of the fitting units 100A through 100F has a frame-shaped outer shape that is approximately rectangular when viewed from above, the frame member 110 may be configured having a different shape, such as a ring shape, a U shape, a C shape, or the like.

In addition, the configuration of the aforementioned sixth embodiment of the present invention is such that the platform unit 200 includes the support column portion 50, and thus the platform unit 200 that includes the support column portion 50 may be provided with a height measurement function. In other words, by adding a configuration that includes a known anthropometer to the support column portion 50 and thus providing a height measurement unit for measuring a height, the configuration may be such that the height of the measurement subject that has stepped onto the platform unit 200 can be measured by the height measurement unit. In such a case, if the configuration is such that height information measured by the height measurement unit provided in the support column portion 50 is inputted into the control unit 10, the height of the measurement subject that has actually been measured can be used as the measurement subject information in various types of computation processes.

Seventh Embodiment

Figure 24:
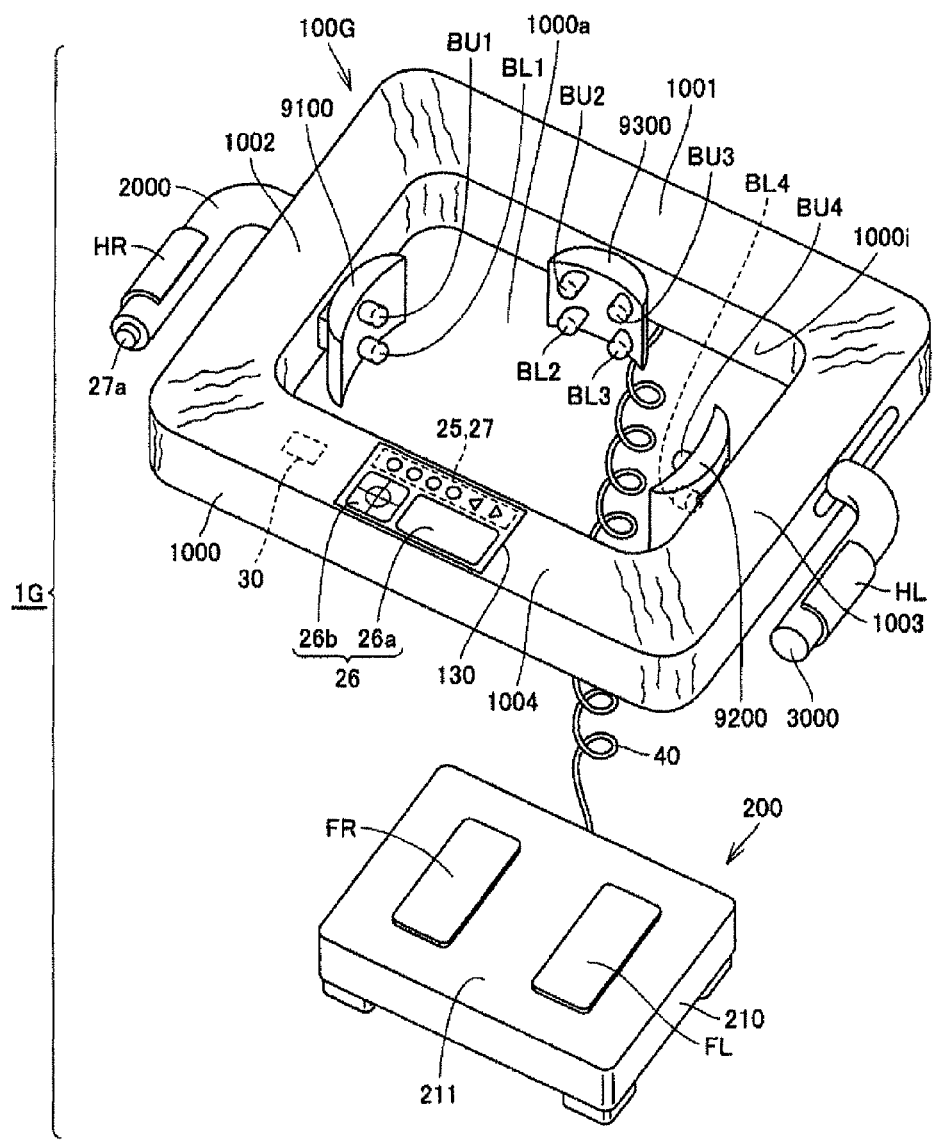
FIG. 24 is a perspective view illustrating a body fat measurement device according to a seventh embodiment of the present invention.
Figure 25:
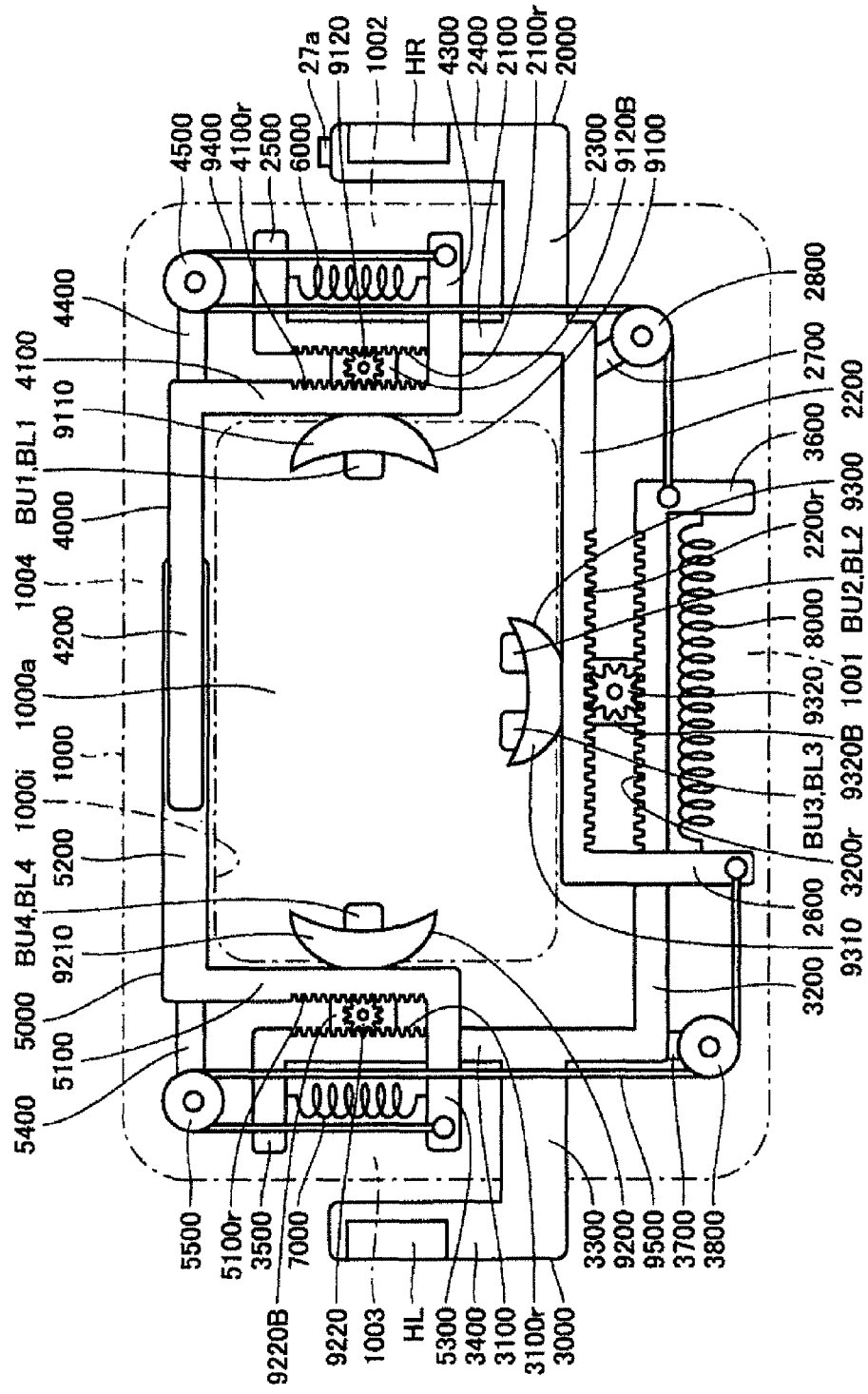
FIG. 25 is a top view of a fitting unit of the body fat measurement device according to the seventh embodiment of the present invention.
Figure 26:
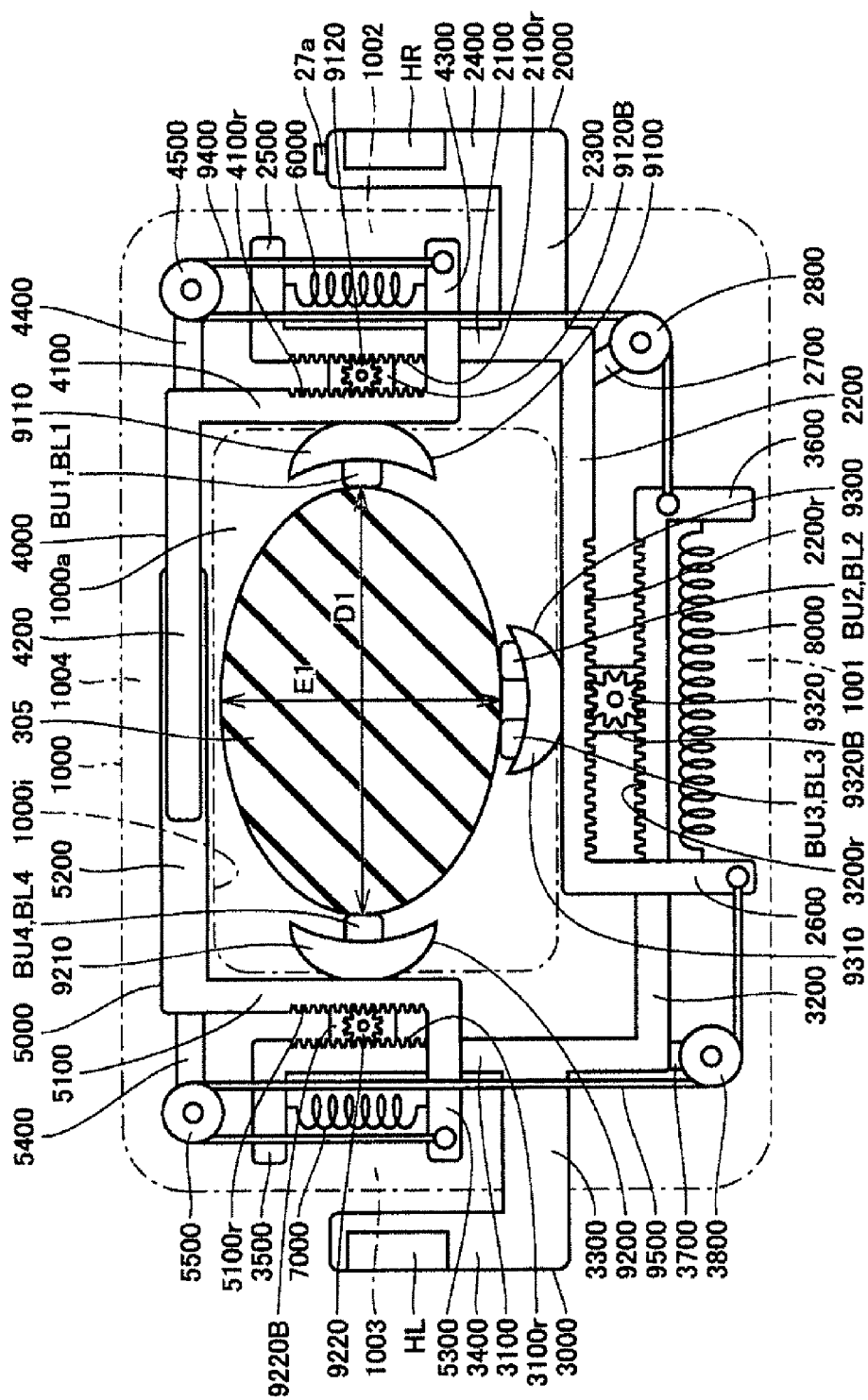
FIG. 26 is a top view illustrating a first measurement state of the fitting unit of the body fat measurement device according to the seventh embodiment of the present invention.
Figure 27:
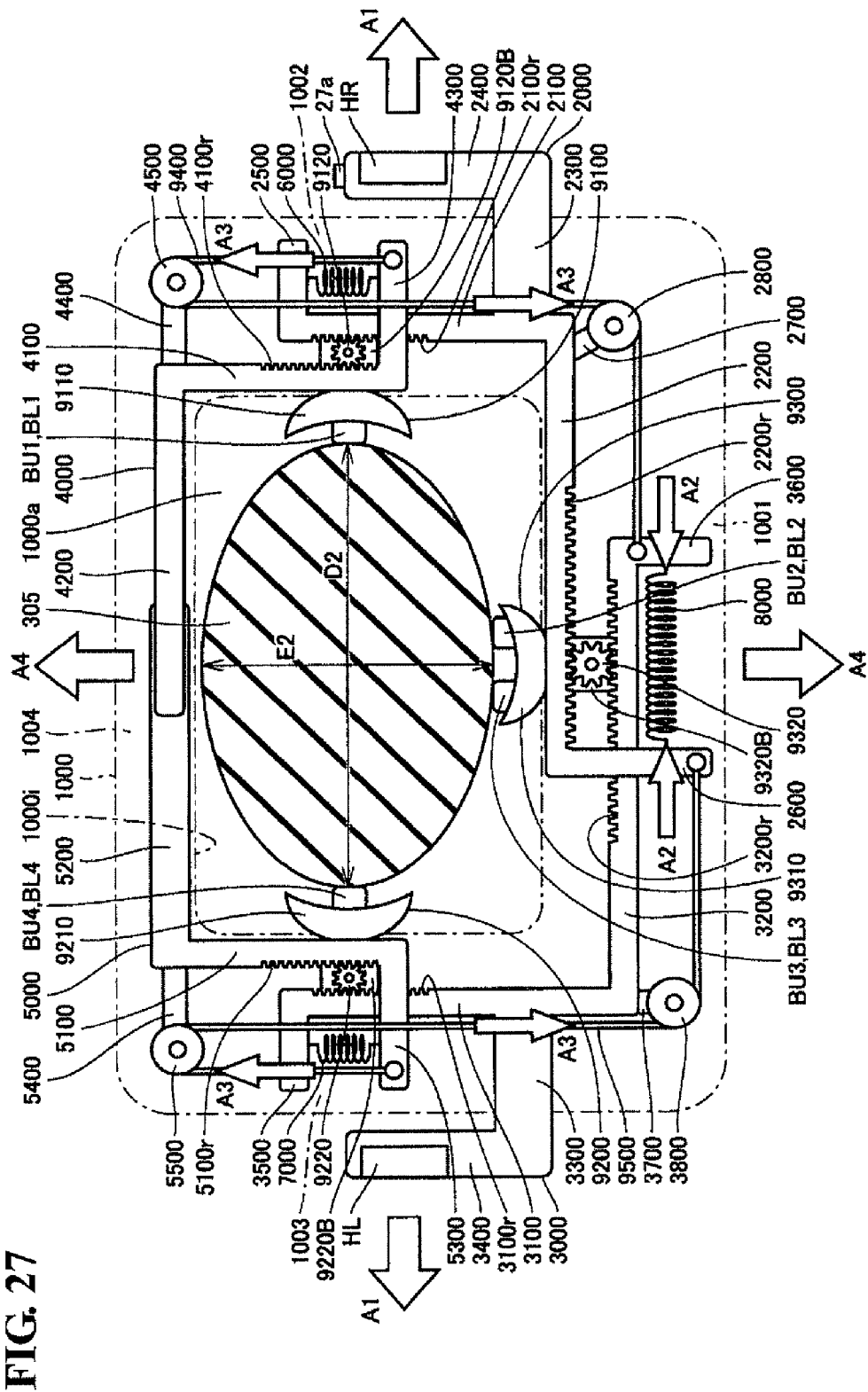
FIG. 27 is a top view illustrating a second measurement state of the fitting unit of the body fat measurement device according to the seventh embodiment of the present invention.
Figure 28:
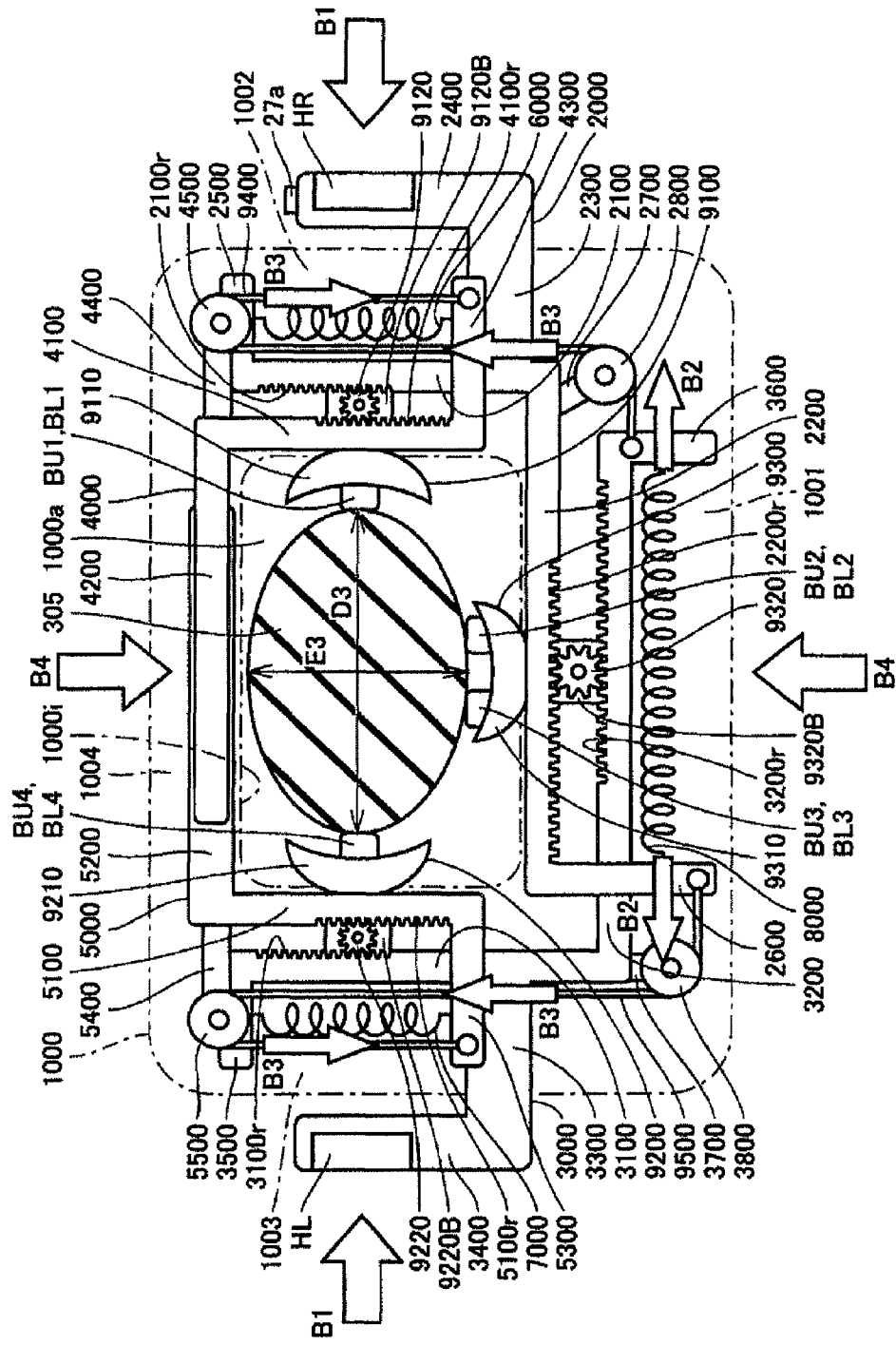
FIG. 28 is a top view illustrating a second measurement state of the fitting unit of the body fat measurement device according to the seventh embodiment of the present invention.

FIG. 24 is a perspective view illustrating a body fat measurement device according to a seventh embodiment of the present invention, FIG. 25 is a top view of a fitting unit of the body fat measurement device according to the seventh embodiment of the present invention, and FIGS. 26 through 28 are top views illustrating first through third measurement states of the fitting unit of the body fat measurement device according to the seventh embodiment of the present invention.

Next, details of the structure of the fitting unit of the body fat measurement device according to the present embodiment, and a fitted state of the fitting unit, will be described with reference to FIGS. 24 through 28. Note that the fundamentals of the measurement performed by the body fat measurement device and the computation processes executed by the control unit according to the present embodiment are the same as those of the body fat measurement devices according to the aforementioned first and second embodiments of the present invention.

As shown in FIG. 24, a body fat measurement device 1G according to the present embodiment includes, like the body fat measurement device 1B according to the aforementioned second embodiment of the present invention, a fitting unit 100G having a circular frame shape capable of being disposed so as to surround the trunk area of the measurement subject in a fitted state, and the platform unit 200 shaped as a platform onto which the measurement subject can step.

The fitting unit 100G of the body fat measurement device 1G according to the present embodiment is configured so that a rear frame portion 1001, a right-side frame portion 1002, a left-side frame portion 1003, and a front frame portion 1004 of a frame member 1000 are connected, and the rear frame portion 1001, the right-side frame portion 1002, the left-side frame portion 1003, and the front frame portion 1004 are each linked to their respective adjacent frame portions so as to be capable of moving relative thereto. An opening 1000a through which the measurement subject passes his/her trunk area is formed in the frame member 1000. With the exception of the internal mechanisms of the frame member 1000, the primary outer surfaces thereof are configured of a flexible member capable of expanding and shrinking.

The display unit portion 130 is provided in an area of the surface of the front frame portion 1004. A right-side driving lever 2000 is exposed from a side area of the right-side frame portion 1002. The hand electrode HR and the measure button 27a are provided on the right-side driving lever 2000. Likewise, a left-side driving lever 3000 is exposed from a side area of the left-side frame portion 1003. The hand electrode HL is provided on the left-side driving lever 3000.

On an inner circumferential surface 1000i of the frame member 1000, a right-side electrode support member 9100 is disposed in the middle of the right-side frame portion 1002, a left-side electrode support member 9200 is disposed in the middle of the left-side frame portion 1003, and a back surface electrode support member 9300 is disposed in the middle of the rear frame portion 1001.

The back area electrodes BU1 and BL1 are provided on the right-side electrode support member 9100, the back area electrodes BU4 and BL4 are provided on the left-side electrode support member 9200, and the back area electrodes BU2, BU3, BL2, and BL3 are provided on the back surface electrode support member 9300. In the present embodiment, the back area electrodes BU1 and BL1 make contact with the measurement subject's right flank and the back area electrodes BU4 and BL4 make contact with the measurement subject's left flank. Hereinafter, the back area electrodes BU1 and BL1 will be referred to as right flank electrodes BU1 and BL1, and the back area electrodes BU4 and BL4 will be referred to as left flank electrodes BU4 and BL4.

The right-side electrode support member 9100, the left-side electrode support member 9200, and the back surface electrode support member 9300 may, like the aforementioned electrode support member 120, be configured of curved plates that are curved so that both ends thereof are positioned forward and the central areas thereof are positioned rearward. The electrodes provided on the right-side electrode support member 9100, the left-side electrode support member 9200, and the back surface electrode support member 9300 are provided so that the surfaces of the electrodes are exposed; it is preferable for the electrodes to protrude slightly from the front surfaces of the respective electrode support members.

The fitting unit 100G includes: a width direction movement linkage mechanism that links outward movement of the right-side frame portion 1002 and the left-side frame portion 1003 with inward movement of the right-side frame portion 1002 and the left-side frame portion 1003; and a depth direction movement linkage mechanism that links outward movement of the front frame portion 1004 and the rear frame portion 1001 and inward movement of the front frame portion 1004 and the rear frame portion 1001.

Meanwhile, the back surface electrode support member 9300 that supports the back area electrodes BU2, BU3, BL2, and BL3 is anchored to the width direction movement linkage mechanism so as to be at a location midway between the right-side frame portion 1002 and the left-side frame portion 1003 even when the right-side frame portion 1002 and left-side frame portion 1003 are moved outward and the right-side frame portion 1002 and left-side frame portion 1003 are moved inward by the width direction movement linkage mechanism.

Meanwhile, the right-side electrode support member 9100 that supports the right flank electrodes B111 and BL1 and the left-side electrode support member 9200 that supports the left flank electrodes BU4 and BL4 are anchored to the depth direction movement linkage mechanism so as to be at a location midway between the front frame portion 1004 and the rear frame portion 1001 even when the front frame portion 1004 and rear frame portion 1001 are moved outward and the front frame portion 1004 and rear frame portion 1001 are moved inward by the depth direction movement linkage mechanism.

Furthermore, the fitting unit 100G according to the present embodiment further includes a depth-width direction movement linkage mechanism that causes the depth direction movement linkage mechanism to move the front frame portion 1004 and the rear frame portion 1001 outward in tandem with the width direction movement linkage mechanism moving the right-side frame portion 1002 and the left-side frame portion 1003 outward, and causes the depth direction movement linkage mechanism to move the front frame portion 1004 and the rear frame portion 1001 inward in tandem with the width direction movement linkage mechanism moving the right-side frame portion 1002 and the left-side frame portion 1003 inward.

In addition, like the body fat measurement device 1B according to the aforementioned second embodiment of the present invention, the body fat measurement device 1G according to the present embodiment does not include a non-contact optical sensor; instead, a movement amount detection sensor that serves as the trunk area width detection unit 24A and detects the amount of movement of the aforementioned right-side frame portion 1002 and the left-side frame portion 1003 relative to the front frame portion 1004 and the rear frame portion 1001, and a movement amount detection sensor that serves as the trunk area depth detection unit 24B and detects the amount of movement of the aforementioned front frame portion 1004 and the rear frame portion 1001 relative to the right-side frame portion 1002 and the left-side frame portion 1003, are provided within the fitting unit 100G. A variety of elements, including various types of encoders such as rotary encoders, optical sensors, magnetic sensors, and so on, can be used as the movement amount detection sensors.

Hereinafter, the width direction movement linkage mechanism, the depth direction movement linkage mechanism, and the depth-width direction movement linkage mechanism employed in the fitting unit 100G will be described in detail with reference to FIG. 25. The right-side driving lever 2000, the left-side driving lever 3000, a right-side slave lever 4000, and a left-side slave lever 5000 are contained within the frame member 1000.

The right-side driving lever 2000 is provided with: a right-side outer frame 2100 that extends in the depth direction; a right-side handle frame 2300 that extends to the right outward from the right-side outer frame 2100 at the rear end side of the right-side outer frame 2100; and a right-side handle 2400 that extends forward from the right-side handle frame 2300. Meanwhile, a right-side first spring engagement frame 2500 is provided at the front end side of the right-side outer frame 2100 so as to extend to the right outward from the right-side outer frame 2100. The hand electrode HR and the measure button 27a are provided on the right-side handle 2400.

A rear-side inner frame 2200 that extends horizontally inward is provided on the opposite side of the right-side outer frame 2100 as the right-side handle frame 2300, and a rear-side first spring engagement frame 2600 that extends rearward is provided at the left end side of the rear-side inner frame 2200. A right-side rear pulley frame 2700 that extends at an angle toward the rear is provided in the vicinity of the location where the rear-side inner frame 2200 and the right-side outer frame 2100 are connected, and a right-side rear pulley 2800 is provided at the leading end of the right-side rear pulley frame 2700.

The left-side driving lever 3000 is provided with: a left-side outer frame 3100 that extends in the depth direction; a left-side handle frame 3300 that extends to the left outward from the left-side outer frame 3100 at the rear end side of the left-side outer frame 3100; and a left-side handle 3400 that extends forward from the left-side handle frame 3300. Meanwhile, a left-side first spring engagement frame 3500 is provided at the front end side of the left-side outer frame 3100 so as to extend to the left outward from the left-side outer frame 3100. The hand electrode HL is provided on the left-side handle 3400.

A rear-side outer frame 3200 that extends horizontally inward and is disposed parallel to the rear-side inner frame 2200 with a predetermined gap provided therebetween is provided on the opposite side of the left-side outer frame 3100 as the left-side handle frame 3300, and a rear-side second spring engagement frame 3600 that extends rearward is provided on the right end side of the rear-side outer frame 3200. A left-side rear pulley frame 3700 that extends at an angle toward the rear is provided in the vicinity of the location where the rear-side outer frame 3200 and the left-side outer frame 3100 are connected, and a left-side rear pulley 3800 is provided at the leading end of the left-side rear pulley frame 3700.

The right-side slave lever 4000 is provided with: a right-side inner frame 4100 that extends in the depth direction and is disposed so as to be parallel with the right-side outer frame 2100 with a predetermined gap provided therebetween; and a right-side second spring engagement frame 4300 that extends to the right outward from the right-side inner frame 4100 at the rear end side of the right-side inner frame 4100. A front-side first frame 4200 that extends to the left inward from the right-side inner frame 4100 is provided at the front end side of the right-side inner frame 4100. A right-side front pulley frame 4400 that extends to the right is provided in the vicinity of the location where the right-side inner frame 4100 and the front-side first frame 4200 are connected, and a right-side front pulley 4500 is provided at the leading end of the right-side front pulley frame 4400.

The left-side slave lever 5000 is provided with: a left-side inner frame 5100 that extends in the depth direction and is disposed so as to be parallel with the left-side outer frame 3100 with a predetermined gap provided therebetween; and a left-side second spring engagement frame 5300 that extends to the left outward from the left-side inner frame 5100 at the rear end side of the left-side inner frame 5100. A front-side second frame 5200 that extends to the left inward from the left-side inner frame 5100 is provided at the front end side of the left-side inner frame 5100. The front-side second frame 5200 is provided so as to contain the front-side first frame 4200 coaxially. A left-side front pulley frame 5400 that extends to the left is provided in the vicinity of the location where the left-side inner frame 5100 and the front-side second frame 5200 are connected, and a left-side front pulley 5500 is provided at the leading end of the left-side front pulley frame 5400.

A right-side outer rack 2100r and a right-side inner rack 4100r are provided on the respective sides of the right-side outer frame 2100 and the right-side inner frame 4100 that face each other. A right-side pinion 9120 that engages with the right-side outer rack 2100r and the right-side inner rack 4100r is provided therebetween. The right-side pinion 9120 is anchored to a right-side base 9210B in a rotatable state. Meanwhile, the right-side electrode support member 9100 is anchored to the right-side base 9210B.

A first spring 6000 is disposed between the right-side first spring engagement frame 2500 and the right-side second spring engagement frame 4300. Furthermore, a first wire 9400 is attached between the rear-side second spring engagement frame 3600 and the right-side second spring engagement frame 4300 so as to be engaged with the right-side front pulley 4500 and the right-side rear pulley 2800.

A left-side outer rack 3100r and a left-side inner rack 5100r are provided on the respective sides of the left-side outer frame 3100 and the left-side inner frame 5100 that face each other. A left-side pinion 9220 that engages with the left-side outer rack 3100r and the left-side inner rack 5100r is provided therebetween. The left-side pinion 9220 is anchored to a left-side base 9220B in a rotatable state. Meanwhile, the left-side electrode support member 9200 is anchored to the left-side base 9220B.

A second spring 7000 is disposed between the left-side first spring engagement frame 3500 and the left-side second spring engagement frame 5300. Furthermore, a second wire 9500 is attached between the rear-side first spring engagement frame 2600 and the left-side second spring engagement frame 5300 so as to be engaged with the left-side front pulley 5500 and the left-side rear pulley 3800.

A rear-side inner rack 2200r and a rear-side outer rack 3200r are provided on the respective sides of the rear-side inner frame 2200 and the rear-side outer frame 3200 that face each other. A rear-side pinion 9320 that engages with the rear-side inner rack 2200r and the rear-side outer rack 3200r is provided therebetween. The rear-side pinion 9320 is anchored to a rear-side base 9320B in a rotatable state. Meanwhile, the back surface electrode support member 9300 is anchored to the rear-side base 9320B.

A third spring 8000 is disposed between the rear-side first spring engagement frame 2600 and the rear-side second spring engagement frame 3600.

Measurement Procedure

Next, a measurement procedure using the fitting unit 100G having the stated configuration will be described with reference to FIGS. 26 through 28. Note that operations of the fitting unit 100G will be described based on the locations of the right-side electrode support member 9100, the left-side electrode support member 9200, and the back surface electrode support member 9300. Note that the measurement procedure to be taken by the measurement subject is the same as the procedure illustrated in FIGS. 6 through 8 and described in the first embodiment, and as the measurement procedure according to the second embodiment.

Standard Body Type

FIG. 26 illustrates measurement performed on a measurement subject having a standard body type. The right flank electrodes BU1 and BL1 supported on the right-side electrode support member 9100 and the left flank electrodes BU4 and BL4 supported on the left-side electrode support member 9200 are pressed against the measurement subject's right flank and the left flank, respectively. Meanwhile, the back area electrodes BU2, BU3, BL2, and BL3 supported on the back surface electrode support member 9300 are pressed against the measurement subject's back area surface.

As shown in FIG. 26, when the fitting unit 100G is in the fitted state, the trunk area 305 of the measurement subject is surrounded by the frame member 1000, and the right flank, left flank, and back area of the trunk area 305 are in contact with the respective electrodes on the fitting unit 100G.

In order to achieve this state, the measurement subject grips the right-side handle 2400 and the left-side handle 3400 with his/her right hand and left hand, respectively, so that the palms of his/her right hand and left hand make contact with the hand electrodes HR and HL, respectively; while maintaining this grip, the measurement subject adjusts the positions of the right-side handle 2400 and the left-side handle 3400 so that the respective electrodes provided in the fitting unit 100G press against the right flank, the left flank, and the back area.

At this time, the measurement subject adjusts the orientation of the fitting unit 100G so that the fitting unit 100G is positioned horizontally, while viewing and referring to the second display unit 26b that displays the orientation of the fitting unit 100G in a visible state. As a result, the fitting unit 100G enters the fitted state shown in FIG. 26, and the measurement of body fat mass can be started.

Here, assuming that the positions of the right-side electrode support member 9100, the left-side electrode support member 9200, and the back surface electrode support member 9300 shown in FIG. 26 are the starting points, the amounts by which the right-side electrode support member 9100, the left-side electrode support member 9200, and the back surface electrode support member 9300 move from the starting points shown in FIG. 26 until those support members reach the positions shown in FIG. 27 or FIG. 28, mentioned later, are measured by the stated movement amount detection sensors, and thus, as shown in FIGS. 26 through 28, the width 2a of the trunk area is calculated as distances D1, D2, and D3, and the depth 2b of the trunk area is calculated as distances E1, E2, and E3.

Large Body Type

A case of a measurement subject having a larger body type than the measurement subject having the standard body type shown in FIG. 26 will now be described with reference to FIG. 27. The measurement subject having this body type grips the right-side handle 2400 and the left-side handle 3400, and moves the right-side handle 2400 and the left-side handle 3400 outward (in the horizontal directions; the directions indicated by A1 in FIG. 27).

Through this, the rear-side first spring engagement frame 2600 and the rear-side second spring engagement frame 3600 move inward (the directions indicated by A2 in FIG. 27) against the biasing force of the third spring 8000. Through this, the first wire 9400 is pulled in the direction indicated by A3 in FIG. 27, and the right-side first spring engagement frame 2500 and the right-side second spring engagement frame 4300 move toward each other against the biasing force of the first spring 6000. Likewise, the second wire 9500 is pulled in the direction indicated by A3 in FIG. 27, and the left-side first spring engagement frame 3500 and the left-side second spring engagement frame 5300 move toward each other against the biasing force of the second spring 7000.

As a result, the right-side electrode support member 9100 moves outward to the right (the direction indicated by A1 in FIG. 27), and the left-side electrode support member 9200 moves outward to the left (the direction indicated by A1 in FIG. 27). Meanwhile, the front-side first frame 4200 and the front-side second frame 5200 also move forward (the direction indicated by A4 in FIG. 27), while the rear-side inner frame 2200 and the rear-side outer frame 3200 also move rearward (the direction indicated by A4 in FIG. 27). As a result, the opening 1000a of the frame member 1000 enlarges, making it possible to perform measurement on the measurement subject who has a large body type.

At this time, the right-side outer rack 2100r and the right-side inner rack 4100r move in different directions, and thus the right-side pinion 9120 does not move in the vertical direction, and instead rotates at that location. As a result, the right-side pinion 9120, the right-side base 9210B, and the right-side electrode support member 9100 do not move in the vertical direction. Through this, even in the case where the front-side first frame 4200 moves forward and the rear-side inner frame 2200 moves rearward, the right-side electrode support member 9100 can stop at a location midway along the depth direction.

Likewise, the left-side outer rack 3100r and the left-side inner rack 5100r move in different directions, and thus the left-side pinion 9220 does not move in the vertical direction, and instead rotates at that location. As a result, the left-side pinion 9220, the left-side base 9220B, and the left-side electrode support member 9200 do not move in the vertical direction. Through this, even in the case where the front-side second frame 5200 moves forward and the rear-side outer frame 3200 moves rearward, the left-side electrode support member 9200 can stop at a location midway along the depth direction.

Likewise, the rear-side inner rack 2200r and the rear-side outer rack 3200r move in different directions, and thus the rear-side pinion 9320 does not move in the horizontal direction, and instead rotates at that location. As a result, the rear-side pinion 9320, the rear-side base 9320B, and the back surface electrode support member 9300 do not move in the horizontal direction. Through this, even in the case where the right-side driving lever 2000 moves to the right and the left-side driving lever 3000 moves to the left, the back surface electrode support member 9300 can stop at a location midway along the horizontal direction.

In this manner, the opening 1000a of the frame member 1000 is enlarged while the right-side electrode support member 9100, the left-side electrode support member 9200, and the back surface electrode support member 9300 are kept in their respective midway locations, and thus even if the measurement subject has a large body type, the back area electrodes BU2, BU3, BL2, and BL3, the right flank electrodes BU1 and BL1, and the left flank electrodes BU4 and BL4 can be pressed against the appropriate locations in the measurement subject's back area surface, right flank, and left flank.

Small Body Type

A case of a measurement subject having a smaller body type than the measurement subject having the standard body type shown in FIG. 26 will now be described with reference to FIG. 28. The measurement subject having this body type grips the right-side handle 2400 and the left-side handle 3400, and moves the right-side handle 2400 and the left-side handle 3400 inward (in the horizontal directions; the directions indicated by B1 in FIG. 28).

Through this, the rear-side first spring engagement frame 2600 and the rear-side second spring engagement frame 3600 move outward (the directions indicated by B2 in FIG. 28) against the biasing force of the third spring 8000. As a result, the first wire 9400 is pulled in the direction indicated by B3 in FIG. 28, and the right-side first spring engagement frame 2500 and the right-side second spring engagement frame 4300 move away from each other against the biasing force of the first spring 6000. Likewise, the second wire 9500 is pulled in the direction indicated by B3 in FIG. 28, and the left-side first spring engagement frame 3500 and the left-side second spring engagement frame 5300 move away from each other against the biasing force of the second spring 7000.

As a result, the right-side electrode support member 9100 moves inward to the left (the direction indicated by B1 in FIG. 28), and the left-side electrode support member 9200 moves inward to the right (the direction indicated by B1 in FIG. 28). Meanwhile, the front-side first frame 4200 and the front-side second frame 5200 also move rearward (the direction indicated by B4 in FIG. 28), while the rear-side inner frame 2200 and the rear-side outer frame 3200 also move forward (the direction indicated by B4 in FIG. 28). As a result, the opening 1000a of the frame member 1000 contracts, making it possible to perform measurement on the measurement subject who has a small body type.

At this time, the right-side outer rack 2100r and the right-side inner rack 4100r move in different directions, and thus the right-side pinion 9120 does not move in the vertical direction, and instead rotates at that location. As a result, the right-side pinion 9120, the right-side base 9210B, and the right-side electrode support member 9100 do not move in the vertical direction. Through this, even in the case where the front-side first frame 4200 moves rearward and the rear-side inner frame 2200 moves forward, the right-side electrode support member 9100 can stop at a location midway along the depth direction.

Likewise, the left-side outer rack 3100r and the left-side inner rack 5100r move in different directions, and thus the left-side pinion 9220 does not move in the vertical direction, and instead rotates at that location. As a result, the left-side pinion 9220, the left-side base 9220B, and the left-side electrode support member 9200 do not move in the vertical direction. Through this, even in the case where the front-side second frame 5200 moves rearward and the rear-side outer frame 3200 moves forward, the left-side electrode support member 9200 can stop at a location midway along the depth direction.

Likewise, the rear-side inner rack 2200r and the rear-side outer rack 3200r move in different directions, and thus the rear-side pinion 9320 does not move in the horizontal direction, and instead rotates at that location. As a result, the rear-side pinion 9320, the rear-side base 9320B, and the back surface electrode support member 9300 do not move in the horizontal direction. Through this, even in the case where the right-side driving lever 2000 moves to the left and the left-side driving lever 3000 moves to the right, the back surface electrode support member 9300 can stop at a location midway along the horizontal direction.

In this manner, the opening 1000a of the frame member 1000 is contracted while the right-side electrode support member 9100, the left-side electrode support member 9200, and the back surface electrode support member 9300 are kept in their respective midway locations, and thus even if the measurement subject has a small body type, the back area electrodes BU2, BU3, BL2, and BL3, the right flank electrodes Bin and BL1, and the left flank electrodes BU4 and BL4 can be pressed against the appropriate locations in the measurement subject's back area surface, right flank, and left flank.

With the body fat measurement device 1G according to the present embodiment as described thus far, the same effects as those described in the aforementioned first embodiment of the present invention can be achieved.

In addition, because the right-side electrode support member 9100, the left-side electrode support member 9200, and the back surface electrode support member 9300 are kept in their respective midway locations, the back area electrodes BU2, BU3, BL2, and BL3, the right flank electrodes BU1 and BL1, and the left flank electrodes BU4 and BL4 can be pressed against the appropriate locations in the measurement subject's back area surface, right flank, and left flank, respectively, regardless of the measurement subject's body type; thus the reliability of the measurement accuracy can be increased.

In addition, in the present embodiment, the state shown in FIG. 25 is employed as a default state using the first spring 6000, the second spring 7000, and the third spring 8000, and thus when the measurement subject is using the body fat measurement device 1G, a force continually acts in the direction that pushes the back area electrodes BU2, BU3, BL2, and BL3, the right flank electrodes BU1 and BL1, and the left flank electrodes BU4 and BL4 against the measurement subject. As a result, the measurement subject can be assisted in taking the measurement, and the burden on the measurement subject can be lightened.

Although the present embodiment employs, as the depth-width direction movement linkage mechanism, a linking mechanism that uses the right-side rear pulley 2800, the right-side front pulley 4500, the first wire 9400, the left-side rear pulley 3800, the left-side front pulley 5500, and the second wire 9500 in order to improve the operability for the measurement subject, it is also possible to employ a configuration in which these elements are not provided.

In addition, in the aforementioned first, second, fifth, sixth, and seventh embodiments of the present invention, the configuration includes the platform unit 200, and thus the platform unit 200 may be provided with a body weight measurement function. In other words, the configuration may be such that a load cell or the like that serves as a body weight measurement unit for detecting a load on the platform unit 200 is provided, which enables the weight of the measurement subject standing on the platform unit 200 to be measured by the body weight measurement unit. In this case, if the configuration is such that body weight information measured by the body weight measurement unit provided in the platform unit 200 is inputted into the control unit 10, the actual measured body weight of the target subject can be used as measurement subject information in the various types of computation processes.

In addition, although the aforementioned first through seventh embodiments of the present invention describe examples in which the computation processes are configured so as to calculate the visceral fat cross-sectional area as the visceral fat mass and the subcutaneous fat cross-sectional area as the subcutaneous fat mass, the computation processes may be configured so that a different indicator than the visceral fat cross-sectional area, such as the visceral fat volume, visceral fat weight, visceral fat level, or the like is calculated as the visceral fat mass, and a different indicator than the subcutaneous fat cross-sectional area, such as the subcutaneous fat volume, subcutaneous fat weight, subcutaneous fat level, or the like is calculated as the subcutaneous fat mass.

In addition, although the aforementioned first through seventh embodiments of the present invention describe examples in which the configuration is such that both the visceral fat cross-sectional area and the subcutaneous fat cross-sectional area are calculated and displayed, the configuration may be such that only one of these indicators is displayed, or that only the subcutaneous fat cross-sectional area is calculated and displayed. Furthermore, the configuration may be such that various types of body composition information aside from the visceral fat cross-sectional area and the subcutaneous fat cross-sectional area (for example, the body fat mass, area-by-area fat mass, fat-free mass, and so on) are calculated and displayed.

In this manner, the embodiments disclosed herein are to be understood in all ways as exemplary and in no ways limiting. The technical scope of the present invention is defined by the appended claims, and all variations that fall within the meaning and range of equivalency of the claims are intended to be embraced therein.

REFERENCE SIGNS LIST 1A, 1B, 1C, 1D, 1E, 1F, 1G body fat measurement device
10 control unit
11 computation processing unit
12 body impedance measurement unit
13 body shape information measurement unit
14 body composition information obtainment unit
14a visceral fat mass calculation unit
14b subcutaneous fat mass calculation unit
21 constant current generation unit
22 terminal switching unit
23 potential difference detection unit
23b, 26b second display unit
24A1, 24A2, 24B1 detection window portion
24A trunk area width detection unit
24B trunk area depth detection unit
25 measurement subject information input unit
26 display unit
26a first display unit
27 operating unit
27a measure button 28 power source unit
29 memory unit
30 unit orientation detection unit
32 level
40, 126A, 126B connection cable
50 support column portion
100A, 100B, 100C, 100D, 100E, 100F, 100G fitting unit
110, 1000 frame member
111, 1001 rear frame portion
112, 1002 right-side frame portion
112a, 113a handle portion
113, 1003 left-side frame portion
114, 1004 front frame portion
115 connection portion
120 electrode support member
121 front surface
125A, 125B electrode pad
130 display unit portion
200 platform unit
210 platform portion
211 top surface
220 support portion
300 measurement subject
301 right foot
302 left foot
303 right hand
304 left hand
305 trunk area
1000a opening
1000i inner circumferential surface
2000 right-side driving lever
2100 right-side outer frame
2100r right-side outer rack
2200 rear-side inner frame
2200r rear-side inner rack
2300 right-side handle frame
2400 right-side handle
2500, 2600, 3500 first spring engagement frame
2700 right-side rear pulley frame
2800 right-side rear pulley
3000 left-side driving lever
3100 left-side outer frame
3100r left-side outer rack
3200 rear-side outer frame
3200r rear-side outer rack
3300 left-side handle frame
3400 left-side handle
3600, 4300, 5300 second spring engagement frame
3700 left-side rear pulley frame
3800 left-side rear pulley
4000 right-side slave lever
4100 right-side inner frame
4100r right-side inner rack
4200 first frame
4400 right-side front pulley frame
4500 right-side front pulley
5000 left-side slave lever
5100 left-side inner frame
5100r left-side inner rack
5200 second frame
5400 left-side front pulley frame
5500 left-side front pulley
6000 first spring
7000 second spring
8000 third spring
9100 right-side electrode support member
9120 right-side pinion
9200 left-side electrode support member
9210B right-side base
9220 left-side pinion
9220B left-side base
9300 back surface electrode support member
9320 rear-side pinion
9320B rear-side base
9400 first wire
9500 second wire
BA1-BA4, BU2-BU3, BL1-BL4, BA1-BA4, BU2-BU3, BL1-BL4 back area electrode
BU1, BL1 back area electrode (right flank electrode)
BU4, BL4 back area electrode (left flank electrode)
FL, FR foot electrode
FL', FR' foot/hip electrode

The invention claimed is:

1. A body fat measurement device comprising:
multiple electrodes for making contact with predetermined areas of a surface of a measurement subject's body;
a trunk area width detection unit configured to measure a trunk area width and a trunk area depth of the measurement subject; and
a controller comprising control logic, which when executed measures a body impedance of the measurement subject's body using the multiple electrodes, and calculates a body fat mass based on the body impedance measured and the trunk area width and trunk area depth detected by the trunk area width detection unit,
wherein the multiple electrodes include at least back area electrodes for making contact with the surface of a back area that corresponds to an area of the measurement subject's trunk area on the back side thereof;
the body fat measurement device further comprises a rigid framed fitting unit that is configured to be disposed so as to surround the measurement subject's trunk area during a fitted state where the measurement subject is in an upright position, is configured to bring the back area electrodes into contact with the measurement subject's back area surface in a pressurized state, and is configured to be movable in at least a vertical direction from a stored state to the fitted state;
the back area electrodes are provided on a surface of the fitting unit in an exposed state, and a display is provided on a surface of the fitting unit disposed on an opposite side of the measurement subject from the back area electrodes in the fitted state, and the back area electrodes are provided on a rear area of the fitting unit so that the surfaces of the back area electrodes that make contact with the back area surface face forward in the fitted state;
the trunk area width detection unit is provided in the fitting unit and is configured of a non-contact range sensor provided on at least one of a right side portion and a left side portion of the fitting unit and a non-contact range sensor provided on a front portion of the fitting unit;
the multiple electrodes further include upper limb electrodes for making contact with the surfaces of the measurement subject's upper limbs; and
the upper limb electrodes are provided on the surface of the fitting unit in an exposed state.

2. The body fat measurement device according to claim 1, further comprising:
a unit orientation detection unit configured to detect an orientation of the fitting unit.

3. The body fat measurement device according to claim 2, wherein the unit orientation detection unit is configured of an accelerometer provided in the fitting unit.

4. The body fat measurement device according to claim 1, wherein a level indicating an orientation of the fitting unit is provided in the fitting unit,
a support column portion that supports the fitting unit so as to be capable of moving along the vertical direction while maintaining the fitting unit in a horizontal orientation.

5. The body fat measurement device according to claim 1, wherein the multiple electrodes further include lower limb electrodes for making contact with the surfaces of the measurement subject's lower limbs;
the body fat measurement device further comprises a platform unit for bringing the lower limb electrodes into contact with the soles of the measurement subject's feet when the measurement subject steps onto the platform unit; and
the lower limb electrodes are provided on a top surface of the platform unit in an exposed state.

6. The body fat measurement device according to claim 5, wherein the platform unit includes a body weight measurement unit that measures the weight of the measurement subject.

7. The body fat measurement device according to claim 1, wherein the multiple electrodes further include lower limb/hip electrodes for making contact with the surfaces of the measurement subject's lower limbs or hip area;
the fitting unit includes extending unit portions for bringing the lower limb/hip electrodes into contact with the surfaces of the lower limbs or hip area by being pulled out from the fitting unit via connection lines; and
the lower limb/hip electrodes are provided on surfaces of the extending unit portions in an exposed state.

8. The body fat measurement device according to claim 1, wherein the controller calculates a visceral fat mass of the measurement subject and a subcutaneous fat mass of the measurement subject.

9. The body fat measurement device according to claim 7, wherein the lower limb/hip electrodes are suspended from the fitting unit by way of the extending unit portions.

10. A body fat measurement device comprising:
multiple electrodes for making contact with predetermined areas of a surface of a measurement subject's body;
a trunk area width detection unit configured to measure a trunk area width and a trunk area depth of the measurement subject; and
a controller comprising control logic, which when executed measures a body impedance of the measurement subject's body using the multiple electrodes, and calculates a body fat mass based on the body impedance measured and the trunk area width and trunk area depth detected by the trunk area width detection unit, wherein
the multiple electrodes include at least back area electrodes for making contact with the surface of a back area that corresponds to an area of the measurement subject's trunk area on the back side thereof;
the body fat measurement device further comprises a rigid framed fitting unit that is configured to be disposed so as to surround the measurement subject's trunk area during a fitted state, and is configured to bring the back area electrodes into contact with the measurement subject's back area surface in a pressurized state;
the back area electrodes are provided on a surface of the fitting unit in an exposed state;
the trunk area width detection unit is provided in the fitting unit;
the multiple electrodes further include upper limb electrodes for making contact with the surfaces of the measurement subject's upper limbs; and
the upper limb electrodes are provided on the surface of the fitting unit in an exposed state
the multiple electrodes further include lower limb/hip electrodes for making contact with the surfaces of the measurement subject's lower limbs or hip area;
the fitting unit includes extending unit portions for bringing the lower limb/hip electrodes into contact with the surfaces of the lower limbs or hip area by being pulled out from the fitting unit via connection lines; and
the lower limb/hip electrodes are provided on surfaces of the extending unit portions in an exposed state, and the lower limb/hip electrodes are suspended from the fitting unit by way of the extending unit portions.

* * * * *